(12) United States Patent
Mayer et al.

(10) Patent No.: US 8,469,025 B2
(45) Date of Patent: Jun. 25, 2013

(54) APPARATUS FOR HUMIDIFYING A RESPIRATORY GAS

(75) Inventors: Wolfgang Mayer, Ebringen (DE); Harald Genger, Starnberg (DE); Stefan Madaus, Gräfelfing (DE); Andreas Klopp, Munich (DE); Stefan Schatzl, Weilheim (DE); Harald Vögele, Gauting (DE); Bernd Lang, Gräfelfing (DE)

(73) Assignee: ResMed R&D Germany GmbH, Martinsried (DE)

( * ) Notice: Subject to any disclaimer, the term of this patent is extended or adjusted under 35 U.S.C. 154(b) by 57 days.

(21) Appl. No.: 12/958,718

(22) Filed: Dec. 2, 2010

(65) Prior Publication Data

US 2011/0073109 A1 Mar. 31, 2011

Related U.S. Application Data

(62) Division of application No. 11/414,432, filed on May 1, 2006, now Pat. No. 7,938,112, which is a division of application No. 10/048,786, filed as application No. PCT/EP00/07602 on Aug. 4, 2000, now Pat. No. 7,096,864.

(30) Foreign Application Priority Data

| Aug. 5, 1999 | (DE) | 199 36 499 |
| Oct. 13, 1999 | (DE) | 199 49 283 |
| Oct. 13, 1999 | (DE) | 199 49 292 |
| Oct. 13, 1999 | (DE) | 299 18 048 |

(51) Int. Cl.
| *A61M 16/00* | (2006.01) |
| *A61M 16/10* | (2006.01) |
| *A61M 16/16* | (2006.01) |
| *A62B 7/00* | (2006.01) |

(52) U.S. Cl.
USPC ............ 128/204.18; 128/203.12; 128/203.17; 128/200.11

(58) Field of Classification Search
USPC ............ 128/200.24, 203.12, 203.16, 203.17, 128/203.19, 203.26, 203.27, 204.14, 204.17, 128/204.18, 204.21
See application file for complete search history.

(56) References Cited

U.S. PATENT DOCUMENTS

| 1,974,843 A | 9/1934 | Blashfield |
| RE19,826 E | 1/1936 | Aisenstein |

(Continued)

FOREIGN PATENT DOCUMENTS

| DE | 275612 | 1/1913 |
| DE | 30 05 094 | 8/1981 |

(Continued)

OTHER PUBLICATIONS

European Search Report mailed Jul. 29, 2004 from Corresponding EP Appln. No. 00953159.1, 6 pgs and 2 pages of English Translation.

(Continued)

*Primary Examiner* — Justine Yu
*Assistant Examiner* — Valerie L Skorupa
(74) *Attorney, Agent, or Firm* — Nixon & Vanderhye P.C.

(57) ABSTRACT

The invention concerns an apparatus for supplying a respiratory gas, a humidifying apparatus, a respiratory gas tube and a connecting apparatus therefor. The apparatus of the invention includes a blowing device for delivering the respiratory gas, a housing device which has a bottom region, a top surface region and a side region extending upwardly between the top surface region and the cover region, as well as a connecting device for connecting a humidifying apparatus for humidifying the respiratory gas, wherein the connecting device is arranged in the side region of the apparatus in such a way that the humidifying apparatus can be laterally coupled thereto. The humidifying apparatus according to the invention is distinguished by a partial amount discharge device for passing a partial amount of the liquid pre-stored in a liquid storage space into a humidifying region. The respiration tube according to the invention includes a connecting plug structure which has both a respiratory gas connecting portion and also a pressure measuring tube connecting portion.

56 Claims, 12 Drawing Sheets

U.S. PATENT DOCUMENTS

| | | | |
|---|---|---|---|
| 2,220,669 A | 11/1940 | Allen | |
| 2,945,619 A | 7/1960 | Ballard | |
| 3,171,353 A | 3/1965 | McMahan | |
| 3,316,910 A | 5/1967 | Davis | |
| 3,584,401 A | 6/1971 | Cryer et al. | |
| 3,612,710 A | 10/1971 | Mount | |
| 3,620,638 A | 11/1971 | Kaye et al. | |
| 3,638,926 A | 2/1972 | Melville et al. | |
| 3,690,317 A | 9/1972 | Millman | |
| 3,789,837 A * | 2/1974 | Philips et al. | 128/202.22 |
| 3,806,102 A | 4/1974 | Valenta et al. | |
| 3,864,440 A | 2/1975 | Giocoechea | |
| 3,873,806 A * | 3/1975 | Schossow | 392/402 |
| 3,954,920 A | 5/1976 | Heath | |
| 4,037,994 A | 7/1977 | Bird | |
| 4,051,205 A * | 9/1977 | Grant | 261/70 |
| 4,105,372 A | 8/1978 | Mishina et al. | |
| 4,171,190 A | 10/1979 | Hudson | |
| 4,222,971 A | 9/1980 | Eilert | |
| 4,229,142 A | 10/1980 | Le Dall et al. | |
| 4,237,080 A | 12/1980 | Elliott | |
| 4,243,396 A | 1/1981 | Cronenberg | |
| 4,336,798 A | 6/1982 | Beran | |
| 4,523,896 A | 6/1985 | Lhenry et al. | |
| 4,532,088 A | 7/1985 | Miller | |
| 4,576,616 A | 3/1986 | Mottram et al. | |
| 4,621,632 A | 11/1986 | Bartels et al. | |
| 4,657,713 A | 4/1987 | Miller | |
| 4,676,237 A | 6/1987 | Wood et al. | |
| 4,753,758 A | 6/1988 | Miller | |
| 4,799,287 A | 1/1989 | Belanger | |
| 4,802,819 A | 2/1989 | Bevington | |
| 4,807,616 A | 2/1989 | Adahan | |
| 4,823,787 A * | 4/1989 | Adahan | 128/203.27 |
| 4,838,258 A | 6/1989 | Dryden et al. | |
| 4,906,417 A | 3/1990 | Gentry | |
| 4,913,140 A | 4/1990 | Orec et al. | |
| 4,921,642 A | 5/1990 | LaTorraca | |
| 4,926,856 A | 5/1990 | Cambio et al. | |
| 4,941,469 A | 7/1990 | Adahan | |
| 4,946,348 A | 8/1990 | Yapp | |
| 4,953,546 A | 9/1990 | Blackmer et al. | |
| 4,973,234 A | 11/1990 | Swenson | |
| 4,993,411 A | 2/1991 | Callaway | |
| 5,097,424 A | 3/1992 | Ginevri et al. | |
| 5,127,800 A | 7/1992 | Hyll et al. | |
| 5,231,979 A | 8/1993 | Rose et al. | |
| 5,237,987 A | 8/1993 | Anderson et al. | |
| 5,271,391 A | 12/1993 | Graves | |
| 5,329,939 A | 7/1994 | Howe | |
| 5,391,063 A | 2/1995 | Hantle et al. | |
| 5,443,061 A | 8/1995 | Champain et al. | |
| 5,445,143 A | 8/1995 | Sims | |
| 5,482,031 A | 1/1996 | Lambert | |
| 5,537,997 A | 7/1996 | Mechlenburg et al. | |
| 5,558,084 A | 9/1996 | Daniell et al. | |
| 5,564,415 A * | 10/1996 | Dobson et al. | 128/204.14 |
| 5,577,496 A | 11/1996 | Blackwood et al. | |
| 5,588,423 A | 12/1996 | Smith | |
| 5,598,837 A | 2/1997 | Sirianne, Jr. et al. | |
| 5,651,775 A | 7/1997 | Walker et al. | |
| 5,655,522 A * | 8/1997 | Mechlenburg et al. | 128/203.12 |
| 5,673,687 A | 10/1997 | Dobson et al. | |
| 5,794,219 A | 8/1998 | Brown | |
| 5,822,715 A | 10/1998 | Worthington et al. | |
| 5,828,943 A | 10/1998 | Brown | |
| 5,832,448 A | 11/1998 | Brown | |
| 5,848,592 A | 12/1998 | Sibley | |
| 5,879,163 A | 3/1999 | Brown et al. | |
| 5,887,133 A | 3/1999 | Brown et al. | |
| 5,888,053 A | 3/1999 | Kobayashi et al. | |
| 5,897,493 A | 4/1999 | Brown | |
| 5,899,855 A | 5/1999 | Brown | |
| 5,913,310 A | 6/1999 | Brown | |
| 5,916,493 A | 6/1999 | Miller et al. | |
| 5,918,603 A | 7/1999 | Brown | |
| 5,933,136 A | 8/1999 | Brown | |
| 5,940,801 A | 8/1999 | Brown | |
| 5,943,473 A | 8/1999 | Levine | |
| 5,951,300 A | 9/1999 | Brown | |
| 5,956,501 A | 9/1999 | Brown | |
| 5,960,403 A | 9/1999 | Brown | |
| 5,985,559 A | 11/1999 | Brown | |
| 5,997,476 A | 12/1999 | Brown | |
| D419,658 S | 1/2000 | Matchett et al. | |
| 6,023,686 A | 2/2000 | Brown | |
| 6,032,119 A | 2/2000 | Brown et al. | |
| 6,101,478 A | 8/2000 | Brown | |
| 6,109,865 A | 8/2000 | Ishikawa | |
| 6,129,524 A | 10/2000 | Woollenweber et al. | |
| 6,131,571 A | 10/2000 | Lampotang et al. | |
| 6,135,432 A | 10/2000 | Hebblewhite et al. | |
| 6,144,837 A | 11/2000 | Quy | |
| 6,158,978 A | 12/2000 | Norbury, Jr. | |
| 6,161,095 A | 12/2000 | Brown | |
| 6,189,870 B1 | 2/2001 | Withall | |
| 6,202,991 B1 | 3/2001 | Coniglio et al. | |
| 6,210,116 B1 | 4/2001 | Kuczaj et al. | |
| 6,213,119 B1 | 4/2001 | Brydon et al. | |
| 6,216,691 B1 | 4/2001 | Kenyon et al. | |
| 6,257,171 B1 | 7/2001 | Rivard | |
| 6,332,462 B1 | 12/2001 | Krohn | |
| 6,349,724 B1 | 2/2002 | Burton et al. | |
| D454,393 S | 3/2002 | Lynch et al. | |
| 6,397,841 B1 * | 6/2002 | Kenyon et al. | 128/202.27 |
| 6,398,197 B1 | 6/2002 | Dickinson et al. | |
| 6,435,180 B1 | 8/2002 | Hewson et al. | |
| 6,471,493 B2 | 10/2002 | Choi et al. | |
| D467,335 S | 12/2002 | Lithgow et al. | |
| D468,011 S | 12/2002 | Lynch et al. | |
| D468,017 S | 12/2002 | McCombs | |
| 6,514,053 B2 | 2/2003 | Takura et al. | |
| 6,543,449 B1 | 4/2003 | Woodring et al. | |
| 6,554,260 B1 | 4/2003 | Lipscombe et al. | |
| 6,604,390 B1 | 8/2003 | Nooner | |
| 6,615,444 B2 | 9/2003 | McGill et al. | |
| 6,622,724 B1 | 9/2003 | Truitt et al. | |
| 6,672,300 B1 | 1/2004 | Grant | |
| D487,311 S | 3/2004 | Lithgow et al. | |
| 6,718,974 B1 | 4/2004 | Moberg | |
| D493,520 S | 7/2004 | Bertinetti et al. | |
| D493,884 S | 8/2004 | Virr et al. | |
| 6,772,999 B2 | 8/2004 | Lipscombe et al. | |
| 6,775,882 B2 | 8/2004 | Murphy et al. | |
| D498,527 S | 11/2004 | Virr et al. | |
| 6,827,340 B2 | 12/2004 | Austin et al. | |
| 6,837,260 B1 | 1/2005 | Kuehn | |
| 6,874,771 B2 | 4/2005 | Birdsell et al. | |
| 6,896,478 B2 | 5/2005 | Botros et al. | |
| 6,910,483 B2 | 6/2005 | Daly et al. | |
| 6,918,389 B2 | 7/2005 | Seakins et al. | |
| 6,935,337 B2 | 8/2005 | Virr et al. | |
| 7,096,864 B1 | 8/2006 | Mayer et al. | |
| 7,111,624 B2 | 9/2006 | Thudor et al. | |
| 7,137,388 B2 | 11/2006 | Virr et al. | |
| 7,413,173 B2 | 8/2008 | DiMatteo et al. | |
| 7,478,635 B2 | 1/2009 | Wixey et al. | |
| 7,614,398 B2 | 11/2009 | Virr et al. | |
| 7,616,871 B2 | 11/2009 | Kramer | |
| 7,677,246 B2 | 3/2010 | Kepler et al. | |
| 2002/0020930 A1 | 2/2002 | Austin et al. | |
| 2002/0056453 A1 | 5/2002 | Klopp et al. | |
| 2002/0159897 A1 | 10/2002 | Kegg et al. | |
| 2003/0062045 A1 | 4/2003 | Woodring et al. | |
| 2003/0084900 A1 | 5/2003 | LeClerc et al. | |
| 2003/0115085 A1 | 6/2003 | Satoh | |
| 2003/0208465 A1 | 11/2003 | Yurko et al. | |
| 2004/0035422 A1 | 2/2004 | Truitt et al. | |
| 2005/0005937 A1 | 1/2005 | Farrugia et al. | |
| 2005/0103339 A1 | 5/2005 | Daly et al. | |
| 2005/0217673 A1 | 10/2005 | Daly et al. | |
| 2006/0191531 A1 | 8/2006 | Mayer | |
| 2006/0237005 A1 | 10/2006 | Virr et al. | |
| 2007/0036662 A1 | 2/2007 | Pesola et al. | |
| 2007/0134085 A1 | 6/2007 | Daly et al. | |
| 2008/0072900 A1 | 3/2008 | Kenyon et al. | |

| | | |
|---|---|---|
| 2010/0192094 A1 | 7/2010 | Jeha et al. |
| 2011/0017212 A1 | 1/2011 | Kenyon et al. |
| 2011/0023877 A1 | 2/2011 | Kenyon et al. |

FOREIGN PATENT DOCUMENTS

| | | |
|---|---|---|
| DE | 36 23 162 A1 | 1/1987 |
| DE | 3642637 | 6/1988 |
| DE | 38 23 242 A1 | 2/1990 |
| DE | 90 14 848.7 | 3/1991 |
| DE | 9014848.7 | 3/1991 |
| DE | 41 38 098 A1 | 5/1993 |
| DE | 42 44 493 A1 | 7/1993 |
| DE | 4244493 A1 | 7/1993 |
| DE | 93 17 450 | 6/1994 |
| DE | 3789221 T2 | 8/1994 |
| DE | 9409231.1 U1 | 12/1994 |
| DE | 195 15 739 A1 | 11/1996 |
| DE | 19630466 | 2/1998 |
| DE | 298 17 685 | 10/1998 |
| DE | 694 09 024 T2 | 10/1998 |
| DE | 19752672 | 3/1999 |
| DE | 29909611 U1 | 10/1999 |
| DE | 10016005 A1 | 12/2001 |
| DE | 20213232 | 4/2003 |
| DE | 102005007773 A1 | 9/2005 |
| EP | 0 201 985 | 11/1986 |
| EP | 0 274 996 B1 | 7/1988 |
| EP | 0274996 | 7/1988 |
| EP | 0589 429 | 3/1994 |
| EP | 0 845 277 A2 | 6/1998 |
| EP | 0 893 750 | 1/1999 |
| EP | 0 903 160 A1 | 3/1999 |
| EP | 1 023 912 A2 | 8/2000 |
| EP | 1 055 431 | 11/2000 |
| EP | 1318307 | 6/2003 |
| EP | 1 374 938 | 1/2004 |
| FR | 2 714 985 | 7/1995 |
| GB | 2069607 A | 8/1981 |
| GB | 2 177 006 A | 1/1987 |
| GB | 2192136 A | 1/1988 |
| GB | 2293325 | 3/1996 |
| GB | 2353904 A | 3/2001 |
| JP | 58-036560 | 3/1983 |
| JP | 5-104681 | 4/1993 |
| JP | 6-190928 | 7/1994 |
| JP | 7-145795 A | 6/1995 |
| JP | 11-398 A | 1/1999 |
| JP | 2000-237316 | 9/2000 |
| JP | 2001-160102 | 6/2001 |
| JP | 2002-206498 A | 7/2002 |
| JP | 2002-253672 | 9/2002 |
| JP | 2002-306601 | 10/2002 |
| WO | WO 93/05451 | 3/1993 |
| WO | WO 95/15778 | 6/1995 |
| WO | WO 97/32619 | 9/1997 |
| WO | WO 98/31937 | 7/1998 |
| WO | WO 98/33433 A1 | 8/1998 |
| WO | WO 98/57691 A1 | 12/1998 |
| WO | WO 99/13932 | 3/1999 |
| WO | WO 99/22793 A1 | 5/1999 |
| WO | WO 99/22794 | 5/1999 |
| WO | WO 99/64747 | 12/1999 |
| WO | WO 00/21602 | 4/2000 |
| WO | WO 00/27457 | 5/2000 |
| WO | WO 00/32261 | 6/2000 |
| WO | WO 00/38771 | 7/2000 |
| WO | WO 00/42324 | 7/2000 |
| WO | WO 01/10489 A2 | 2/2001 |
| WO | WO 01/32069 | 5/2001 |
| WO | WO 01/73653 A1 | 10/2001 |
| WO | WO 02/02169 A1 | 1/2002 |
| WO | WO 02/066107 A1 | 8/2002 |
| WO | WO 2007/019628 | 2/2007 |
| WO | WO 2009/059359 | 5/2009 |
| WO | WO 2009/156921 A1 | 12/2009 |
| WO | WO 2010/092496 | 8/2010 |

OTHER PUBLICATIONS

Notice of Reasons for Rejection mailed Dec. 15, 2009 in Japanese Appln. No. 2006-515536, together with an English translation.
Breas Medical AB, "iSleep® 20", Dec. 2007, 2 pages.
De Vilbiss® Healthcare, "DeVilbiss IntelliPAP® Standard CPAP System," Nov. 2007, 2 pages.
Fisher & Paykel Healthcare, Specification Sheet for "SleepStyle™ 200 CPAP Series," 2005, 4 pages.
Fisher & Paykel Healthcare, Specification Sheet for "SleepStyle™ 600 CPAP Series," 2005, 4 pages.
Hoffrichter GmbH, "VECTOR Therapy in Perfection," 2002, 2 pages.
Fisher & Paykel Healthcare, "Two Easy Steps to Comfort, Humidification and Nasal CPAP Therapy," Aug. 1995, 4 pages.
MAP Medizin-Technologie GmbH, "minni Max nCPAP, The Respiratory Therapy Device With•Out an Integrated Humidifier," Dec. 2003, 17 pages.
MAP Medizintechnik fuer Arzt and Patient, maxII nCPAP moritzII biLEVEL, "The gentle Therapy for Sleep-Related Breathing Disorders," 2000, 4 pages.
Respironics Inc., "System One Heated Humidifier User Manual," May 2009, 20 pages.
ResMed, "The Sullivan® HumidAire™," 1997, 1 page.
Japanese Office Action mailed Mar. 23, 2010 in Japanese Appln. No. 2001-515003.
Fisher & Paykel Healthcare "SleepStyle™ 200 CPAP Series" Specification Sheet, 1998, 4 pages.
Madaus Schwarzer Medizintechnik, "New Approaches in Diagnosis and Therapy—Moritz biLevel User Manual", May 1994, 38 pages.
Hoffrichter "Vector CPAP—Therapy With Technical Mastery", 4 pages, Oct. 1998.
German Patent Manual for Hoffrichter/Sandmann CPAP Respirator—Perfect CPAP Therapy, 30 pages plus Translation Verification Certificate, Mar. 1998.
European Search Report mailed Dec. 17, 2012 in European Application No. 10185455.2, with English translation of the European Search Opinion (14 pages).
European Search Report mailed Dec. 14, 2012 in European Application No. 10185462.8, with English translation of the European Search Opinion (10 pages).

* cited by examiner

APPARATUS FOR HUMIDIFYING A RESPIRATORY GAS

CROSS REFERENCE TO RELATED APPLICATIONS

This application is a divisional of U.S. application Ser. No. 11/414,432, filed May 1, 2006, pending, which is a divisional of U.S. application Ser. No. 10/048,786, filed Aug. 6, 2002, now U.S. Pat. No. 7,096,864, which is the National Phase of International Application PCT/EP00/07602, filed Aug. 4, 2000, which designated the U.S., each of which is incorporated herein by reference in its entirety.

BACKGROUND OF THE INVENTION

1. Field of the Invention

The invention concerns an apparatus for supplying a respiratory gas under an increased pressure comprising a blowing device for delivering the respiratory gas, a housing device for receiving the blowing device and a connecting device for connection of a humidifying apparatus for humidifying the respiratory gas delivered by the delivery device. The invention further concerns a humidifying apparatus for humidifying a respiratory gas as well as a respiratory gas tube or hose and a connecting apparatus therefor.

2. Description of Related Art

Apparatuses for supplying a respiratory gas under an increased pressure are used in particular in the field of sleep therapy for dealing with sleep-related respiratory disturbances. Supplying the respiratory gas under a predetermined increased pressure, usually in the range of between 5 and 20 mbar, provides for pneumatic splinting of the upper respiratory tracts of a patient, in a physiologically well compatible fashion, whereby it is possible to effectively prevent obstruction in that respiratory tract region.

Usually the respiratory gas is formed directly from the ambient air which is preferably sucked in by way of a filter device. In dependence on the climatic conditions which fluctuate in particular due to the time of year involved, it has proven to be advantageous for the respiratory gas which is supplied to the patient, for example by way of a blowing device, under a regulated, possibly alternating pressure, to be humidified from time to time. For that purpose it is possible to insert a humidifying device into the respiratory gas path between the blowing device and the respiratory mask, for example by way of an intermediate hose portion. CPAP-units with an integrated humidifying apparatus are also known.

In the case of the humidifying apparatuses which are only inserted into a hose line however, there is frequently the problem of inadequate strength and stability. In the case of CPAP-units with an integrated humidifying apparatus the latter has to be constantly taken around, even if there is temporarily no need for humidification of the respiratory gas.

SUMMARY OF THE INVENTION

Under the impulsion of that problem, the object of the invention is to provide an apparatus for supplying a respiratory gas and a humidifying apparatus which is provided for same, which is robust and simple to handle and which can be configured in an easy fashion according to respective requirements involved.

In accordance with the invention that object is attained by an apparatus for supplying a respiratory gas, having one or more features described below.

By virtue thereof, it is advantageously possible for a humidifying apparatus to be coupled directly laterally to a CPAP-unit easily and without the need for expert assembly procedures, and without the CPAP-unit having to be lifted for that purpose. In that case the lower support portions by way of which the CPAP-unit is set up advantageously act directly as a guide device which permits the humidifying apparatus to be easily pushed to the CPAP-unit. If for example there is temporarily no need for a humidifying apparatus or if the humidifying apparatus is to be temporarily separated from the CPAP-unit for cleaning purposes, the CPAP-unit can remain unchanged at the location at which it is set up and the humidifying apparatus can simply be removed towards the side, in particular by being pulled off.

In accordance with a particularly preferred embodiment of the invention the connecting members are oriented substantially in the joining direction. In particular the main passage cross-section for the respiratory gas which is delivered by the blowing device is advantageously formed by a tube connection, on to which can be fitted a connecting portion which is provided on a humidifying apparatus of correspondingly complementary configuration.

An embodiment of the invention which is particularly advantageous from esthetic points of view and in regard to a symmetrical structure for the CPAP-unit system is afforded if the corresponding connecting members are provided in an end (front side) of the unit. The surface portion of that end of the unit is of a substantially complementary configuration to a portion of the humidifying apparatus, which is adjacent in the joined position.

An embodiment of the invention which is advantageous in particular in regard to particularly reliable coupling of a pressure measuring conduit is afforded if the connecting device has said tube connection for conducting the respiratory gas therethrough and a conduit portion which is arranged adjacent thereto, for coupling a pressure-measuring conduit.

The tube connection for passing the respiratory gas therethrough and the conduit portion for the pressure measuring conduit, in accordance with a particularly preferred embodiment of the invention, are arranged in an opening in such a way that they do not project substantially beyond a main plane defined by the front end face of the unit. That affords particularly effective protection for these comparatively filigree CPAP-unit connecting members.

In accordance with a particular aspect of the present invention the connecting device, for connection of the humidifying apparatus as required, includes electrical connecting members for affording an electrical connection to the humidifying apparatus. By way of those electrical connecting members it is advantageously possible to supply voltage to a heating device of the humidifying apparatus, without a corresponding voltage supply cable having to be manually connected for that purpose to the humidifying apparatus. The electrical connecting members can also be used for the transmission of electrical signals, for example for the transmission of a filling level signal or also for the transmission of electrical signals which are supplied for example in the region of the respiratory tube connecting device.

A particularly effective coupling for the CPAP-unit to the humidifying apparatus which is intended for connection thereto is achieved in accordance with the invention in that there is provided a latching device which can be manually put into a release position and which holds the humidifying apparatus in a joined position. By virtue of that arrangement it is advantageously possible for the humidifying apparatus to be designed in such a way as to save a great deal of weight, without in that respect involving the risk that it is by mistake pulled off the CPAP-unit by way of the connected respiratory gas tube or hose and caused to fall off the surface on which it is supported (for example an occasional table).

In accordance with a particularly preferred embodiment of the invention the CPAP-unit is designed in the bottom region in such a way that the connecting members and in particular the above-mentioned tube connection are arranged at a vertical heightwise level which exactly corresponds to the heightwise level of the connecting members provided on the humidifying apparatus.

Advantageously, the connecting members provided on the CPAP-unit and also those on the humidifying apparatus are positioned in a vertical direction in such a way that, when the CPAP-unit and the humidifying apparatus are set up on a substantially flat support, the humidifying apparatus can be pushed to the CPAP-unit, in which case the required orientation of those two modules in the vertical direction is already achieved by virtue of the surface on which they are standing. In order also to attain sufficient centering of the two modules in the lateral direction, centering aids are also provided in accordance with a particularly preferred embodiment of the invention. In that respect, a particularly robust centering aid is achieved if the inside wall of the opening which receives the tube connection is matched to the outside peripheral surface of the connecting projection provided on the humidifying apparatus.

In regard to the humidifying apparatus the object set forth hereinbefore is attained by a humidifying apparatus having one or more of the features described below. Such a humidifying apparatus can be coupled in a simple fashion to a suitable CPAP-unit, even by a lay person, without expert assembly procedures or a connecting tube or hose being required for that purpose. The CPAP-unit does not have to be lifted for that purpose.

Advantageously there is provided a humidifier unit which can be coupled to a base unit and which includes a cartridge-like refilling module which can be removed and re-fitted. The refilling module can be fixed in the humidifier unit by way of fixing devices, for example a bayonet fixing device. The refilling module can be sealed off in a portion-wise manner or completely in the humidifier unit by sealing devices.

In the context of a CPAP-therapy, spontaneous respiration of a patient is assisted by a respiratory gas under permanent increased pressure being supplied to the patient. That increased pressure affords pneumatic splinting of the upper respiratory tracts, whereby it is possible to obviate any respiratory tract obstructions which occur during a patient sleep phase. In the treatment of sleep-related respiratory disturbances in that manner, that increased-pressure artificial respiration usually extends over the entire sleep phase of the patient. In regard to improved physiological compatibility of that increased-pressure artificial respiration it has proven to be advantageous to humidify the respiratory gas which is fed to the patient. Usually, humidification of the respiratory gas is effected by the respiratory gas being passed over a water bath and in so doing absorbing moisture. An amount of water of about 750 ml is usually stored in that water bath. The water bath is preferably slightly heated by means of a heating device. When using those conventional humidifying apparatuses, it has been found that the absolute moisture content of the respiratory gas, as viewed over the entire sleep phase, is subject to in part considerable fluctuations.

To resolve that problem, in accordance with a particular aspect of the present invention, there is described an apparatus, which is simple to handle, for the humidification of a respiratory gas, and a CPAP-unit which is intended for use therewith, by means of which it is possible to achieve uniform humidification of the respiratory gas. That is achieved by an apparatus for the humidification of a respiratory gas comprising a liquid storage space for storage of a liquid, a humidifying region for loading the respiratory gas with the liquid by the respiratory gas coming into contact in the humidifying region with the liquid, a respiratory gas supply device for supplying the respiratory gas to the humidifying region, and a respiratory gas withdrawal device for withdrawal of the humidified respiratory gas from the humidifying region, wherein there is provided a partial-amount discharge device for passing only a partial amount of the liquid stored in the liquid storage space into the humidifying region.

That arrangement makes it advantageously possible to provide a respiratory gas which is humidified according to the respective requirements involved, just a short time after the unit is brought into operation. With a desired heating effect for the humidifying medium, that can be achieved quickly and with a comparatively low level of power draw. As a result of the low level of power draw of the heating device the humidifying apparatus according to the invention is particularly suitable for operation independently of a mains network, by means of a battery or an accumulator.

In accordance with a particularly preferred embodiment of the invention the humidifying region is spatially separated from the liquid storage space. In order for supplying the humidifying medium from the liquid storage space, according to the respective requirements involved, there is preferably provided a fluid conduit device by way of which the humidifying region is in communication with the liquid storage space.

Provided between the humidifying region and the liquid storage space, in accordance with a preferred embodiment of the invention, is a separating wall which separates the humidifying region from the liquid storage space. The fluid conduit device is preferably arranged in such a way that it passes through the separating wall.

An embodiment of the invention which is advantageous in terms of particularly advantageous handleability and reliable filling of the humidifying region is afforded if the liquid storage space is arranged above the humidifying region in the position of use of the apparatus. By virtue of that arrangement, it is possible for the humidifying medium to be passed into the humidifying region as a result of the force of gravity acting thereon. The discharge of a partial amount of the liquid into the humidifying region is advantageously effected in dependence on a level of liquid in the humidifying region. In that way it is possible for a given minimum amount of humidifying liquid to be kept permanently available in the humidifying region.

The filling level in the humidifying region is advantageously quantitatively controlled by the introduction of air into the liquid storage space, for the discharge of a partial amount of the liquid out of the liquid storage space. For that purpose, in accordance with a particularly preferred embodiment, the air for introduction into the liquid storage space is drawn in by way of the humidifying region.

Control of the supply of air is preferably effected by the provision of a metering or quantitative control conduit device which extends between the liquid storage space and the humidifying region, wherein the conduit device has a first mouth opening which is at the height of the level of liquid in the humidifying region and a second mouth opening which opens into the liquid storage space into a region above the level of liquid in the storage space. In that situation the first mouth opening is covered by the liquid disposed in the humidifying region until the level of liquid falls below the first mouth opening. As soon as the first mouth opening is cleared air can then flow into the liquid storage space by way of the quantitative control conduit device. As the result of that make-up flow of air, a small amount of fluid again passes into the humidifying region and the level of the liquid in the humidifying region rises until the first mouth opening is again below the level of the liquid.

The quantitative control conduit device is advantageously formed by a tube conduit which passes through the separating wall in a vertical direction.

The liquid is transferred from the liquid storage space into the humidifying region through a tube projection portion which extends from the separating wall into a region below the first mouth opening of the quantitative control conduit device or the air-introduction conduit device.

An embodiment of the humidifier which is robust and advantageous in terms of manufacture from production-engineering points of view is afforded by the separating wall and the two fluid conduit devices being of an integral nature.

The liquid storage space is preferably formed by a cup-shaped housing portion. That housing portion is preferably formed from a transparent or translucent material. Making the housing portion from a plastic material advantageously provides for protection from splintering and a still further reduction in the level of heat losses.

In accordance with a particularly preferred embodiment of the invention the humidifying region is formed in a trough or vat element. Particularly effective humidification of the respiration gas, with a structure which is still compact, can advantageously be achieved by the provision of air conduit devices which are arranged in such a way that air flows through the trough element substantially transversely or along a spiral path. That provides intensive contact of the respiratory gas with the partial amount of liquid accommodated in the humidifying region.

Particularly intensive humidification of the respiratory gas can be achieved by the provision of a heating device for heating the partial amount of liquid stored in the humidifying region. The heating device is preferably operated electrically, for example by a resistance heating means. The resistance heating means is preferably formed by a thin foil-like element thermally coupled to a bottom region of the trough element. For that purpose preferably the trough element has a bottom portion which is formed from a material of high thermal conductivity, in particular metal. As an alternative thereto or also in combination therewith, it is also possible for the heating device to be integrated directly into a wall portion, in particular a bottom portion, of the humidifying region.

Advantageously the integral member forming the separating wall is fitted in sealing relationship into the trough element by way of a first peripheral sealing device. The integral member preferably also includes a second peripheral sealing device which closes the liquid storage space in sealing relationship, in conjunction with the separating wall. The humidifying unit which is formed in that way can be opened for the refilling procedure by the trough element being removed from the housing portion which forms the liquid storage space.

In accordance with a particularly preferred embodiment of the invention, to receive the described humidifying unit there is provided a support or installation housing into which at least the trough element can be fitted. Advantageously the trough element or the support housing is provided with a respiration tube connecting device for the connection of a respiration tube. In accordance with a particularly preferred embodiment of the invention there is provided a secondary or duplicate tube connecting device in the region of the respiration tube connecting device. By way of a secondary tube of preferably small diameter, which can be connected to the secondary tube connecting device, it is possible to implement pressure measurement in a region following the humidifying apparatus, for example in the region of a $CO_2$ exchange valve. The secondary tube connecting device is preferably arranged immediately beside a respiratory tube connecting projection. Advantageously the connecting structure provided on the humidifying apparatus for the respiration tube and preferably also for the secondary tube and in particular the pressure-measuring tube corresponds in respect of its constitution to the connecting structure correspondingly provided on a CPAP-unit. That advantageously provides for compatibility of the tube connections both with the CPAP-unit and also with the humidifying device which is possibly connected therebetween.

In that respect, a robust embodiment which is advantageous from the points of view of production engineering is afforded if the secondary tube connecting device and the respiration tube connecting device are formed integrally with the trough element or with the support housing.

In a particularly preferred embodiment of the invention the humidifying apparatus has connecting members which permit direct docking of the humidifying apparatus to a corresponding CPAP-unit.

For that purpose in accordance with a particularly preferred embodiment of the invention the CPAP-unit and the humidifying apparatus are so designed that they can be reliably and securely coupled. That arrangement preferably also entails coupling of the duplicate or secondary tube connecting device provided on the humidifying apparatus, to a connecting device provided on the CPAP-unit.

Independently of the measures described hereinbefore or also advantageously in combination therewith, the above-identified object in accordance with the invention is also attained by an apparatus for humidifying a respiratory gas comprising a liquid storage space for storing a liquid, a humidifying region for loading the respiratory gas with the liquid by the respiratory gas coming into contact in the humidifying region with the liquid, a respiratory gas supply device for supplying the respiratory gas to the humidifying region and a respiratory gas withdrawal device for withdrawal of the humidified respiratory gas from the humidifying region, wherein the liquid storage space is formed by a housing portion which is coupled to a trough element to form the humidifying region and there is provided a support or installation housing portion for receiving a unit formed by the housing portion and the trough element.

In terms of a CPAP-unit the object as set forth in the opening part of this specification is attained by a CPAP-unit comprising an outer housing, a conveyor device accommodated in the outer housing for conveying a respiratory gas to a respiratory gas outlet connection, a pressure-detection device, a control device for controlling the conveyor device in dependence on the detected pressure and a pressure-measuring connection for the connection of a pressure-detection conduit, wherein the respiratory gas outlet connection and the pressure-measuring connection are of a complementary configuration to connecting members provided on the humidifier side.

That advantageously affords a CPAP-system of a modular structure, which can be easily and quickly configured according to the respective requirements involved, even by a lay person. The CPAP-unit system according to the invention is also distinguished, in a completely dismantled condition, by a high level of complexity and in addition can be transported in the form of a stable unit.

The invention further concerns a respiration tube connecting device for coupling a respiration tube formed from a flexible material to a CPAP-unit and a respiration tube provided with a corresponding connecting device.

Respiration tubes of that kind are used in particular in the therapy of sleep-related respiration disturbances. In that situation the respiratory gas is supplied to a patient under a predetermined increased pressure which possibly alternates during a respiration cycle, to provide for a pneumatic splinting effect for the upper respiratory tracts.

To control the respiratory gas pressure, it is known to detect by way of a pressure-measuring tube the pressure in the region of a respiratory mask or in a region which is preferably spaced therefrom by between about 10 and 15 times the inside diameter of the respiratory gas tube. That pressure-measuring tube is usually inserted into the respiration tube.

The respiration tube can be fitted directly or by way of an elastic connecting plug sleeve on to a connecting projection provided on a CPAP-unit. In that case the pressure-measuring tube is either fitted by plugging engagement on to a tube portion provided in coaxial relationship in the interior of the connecting projection or it is passed out of same by way of a small hole provided in the respiration tube and fitted in plugging engagement separately on to a corresponding pressure-detection connecting projection provided on the CPAP-unit. The known respiration tube connecting structures with integrated connecting members for a pressure-measuring tube involve the problem of a comparatively high level of respiratory resistance and difficulties in cleaning. Systems with a pressure-measuring tube which is passed freely out of same suffer from the problem that the connection of the pressure-measuring tube is forgotten under some circumstances so that this can result in an unacceptably high rise in pressure in terms of the respiratory gas feed.

Having regard to those circumstances and in accordance with a further concept of a way of attaining the object of the invention, there is provided a robust respiration tube system which is easy to handle and which is distinguished by involving a comparatively low level of respiratory resistance and with which correct coupling of the respiration tube to a CPAP-unit is guaranteed even without particular attention being paid.

In accordance with the invention that is attained by a respiration tube connecting apparatus having a base body, a respiratory gas passage duct formed in the base body, and a respiration tube connection portion for receiving an end portion of a respiration tube, which is distinguished in that provided in the base body in a region which is radially displaced with respect to the center of the respiratory gas passage duct is an additional coupling portion for coupling of an additional hose conduit to a complementary connecting structure provided on a respiratory gas source.

The base body is preferably formed from an elastomer material, whereby it is possible to provide for particularly reliable sealing integrity with the complementary connecting structure and adequate fixing of the plug connection.

The above-mentioned tube conduit connected to the additional coupling portion generally involves a pressure-measuring conduit. That additional tube conduit however may also be in the form of an analysis conduit for taking a respiratory gas sample or in the form of a flushing conduit for the exchange of consumed respiratory gas or also in the form of a feed conduit for example for oxygen.

In accordance with a particularly preferred embodiment of the invention the passage cross-section of the respiratory gas passage duct substantially corresponds to the passage cross-section of the respiration tube. That advantageously ensures that the connecting plug does not contribute to a considerable degree to an increase in respiratory resistance.

The respiratory gas passage duct is preferably of a substantially circular cross-section and can be fitted with an easy press fit on to a connecting projection provided at the unit. Preferably the respiratory gas passage duct is of such a configuration, in its region which can be pushed on to the connecting projection, that the inside wall of the connecting projection adjoins substantially steplessly the inside wall of the following region of the respiratory gas passage duct.

The additional coupling portion is preferably formed by a cylindrical bore portion which is provided in the base body and which extends substantially parallel to the longitudinal center line of the respiratory gas passage duct. The inside diameter of the respiratory gas passage duct is preferably in the region of between 15 and 24 mm, preferably 19 mm—the inside diameter of the additional coupling portion is in the region of between 3 and 8 mm, preferably being 4 mm.

An embodiment of the invention which is particularly advantageous in terms of handling is preferably afforded if extending in the interior of the base body is a duct portion which leads from the additional coupling portion into the respiratory gas passage duct. The duct portion is preferably of a cross-section which is sufficient to receive the additional tube conduit.

Advantageously the additional tube conduit is inserted into the duct portion in sealing relationship, preferably being secured therein by adhesive. The additional tube conduit is preferably passed through the duct portion as far as a front end of the base body and introduced into the coupling portion.

A respiration tube fixing portion is advantageously formed in a region which is remote from the front end of the base body, wherein the respiration tube is fixed in the respiration tube fixing portion in sealing relationship, in particular being secured therein by adhesive or vulcanisation. As an alternative thereto or also in combination with those measures, it is also possible to provide in the respiration tube fixing portion a zone with a female screwthread, which is complementary in shape to the outside peripheral surface of a respiration tube which has a spiral insert.

In accordance with a preferred embodiment of the invention, towards the respiration tube, the inside region of the respiratory gas passage duct is also of such a configuration as to provide a substantially stepless transition into the respiration tube. That also achieves an effective reduction in respiratory resistance.

A particularly secure and load-bearing coupling between the respiration tube and the connecting plug structure is achieved by the base portion being injection-molded to the respiration tube and/or the additional tube conduit. The base body is preferably formed from an in particular transparent or translucent elastomer material, in particular silicone rubber.

The described connecting structure advantageously provides a respiration tube for a CPAP-unit, with a tube body which is formed from a flexible material, a pressure-measuring tube which is guided in the tube body, and a connecting plug structure provided at the end of the tube body, wherein the connecting plug structure is formed from an elastomer material and provided in the connecting plug structure is a duct portion by way of which the pressure-measuring tube is passed out of a respiratory gas conduit region into a coupling portion which is disposed laterally beside a respiratory gas conduit portion.

The region of the connecting plug structure which accommodates the coupling portion preferably projects in a nose-like configuration radially beyond an outside peripheral surface of the respiration tube connecting portion, whereby it is possible to achieve particularly effective pre-positioning of the plug.

For the treatment of sleep-related respiratory disturbances it is known to feed a patient with a respiratory gas which is optionally humidified, under a predetermined increased pressure. In that respect, in most cases the provision of the respiratory gas under an increased pressure is effected by way of blowers which are regulated in respect of their rotary speed. Those blowers are usually accommodated in a preferably sound-insulated housing portion and are connected to a conduit system which leads to a humidifying device or directly to a coupling portion for the connection of a respiration tube. That coupling portion is generally in the form of a short tube connecting projection portion on to which the respiration tube can be fitted in sealing relationship.

Particularly in the case of CPAP-units for affording comparatively high respiratory gas pressure levels, it has been found to be advantageous to detect the instantaneous pressure in the respiration tube or within a respiration mask. That purpose is usually implemented by using a pressure-measuring tube, by way of which the pressure to be monitored is taken off at a defined measuring location and fed to a pressure transducer which for example is integrated into the CPAP-unit. In that case the pressure-measuring tube is fitted in sealing relationship on to a connecting projection, in a similar manner to the respiration tube. Compatibility problems frequently arise here, having regard to the large number of widely used respiration tube, pressure-measuring tube and humidifying systems.

In accordance with a further concept of the invention that is attained by a connecting structural component for a CPAP-unit having a tubular respiration gas conduction device whose passage cross-section substantially corresponds to the passage cross-section of a respiration tube provided for connection thereto, and a pressure-measuring tube connecting device for the connection of a pressure-measuring tube, wherein the respiration gas conduction device and the pressure-measuring connecting device are arranged in mutually juxtaposed relationship.

It is advantageously possible in that way for a conventional respiration tube, a conventional pressure-measuring tube or also a respiration tube with a combination plug assembly, to be connected to the correspondingly designed CPAP-unit.

The respiratory gas conduction device is preferably formed by a tube connecting projection whose inside diameter substantially corresponds to the inside diameter of a respiration tube. The pressure-measuring tube connecting device is also preferably formed by a tube connecting projection. Particularly effective protection for the two tube connecting projections is afforded by the two tube connecting projections being arranged in sunk relationship in an opening.

A particularly robust embodiment of the invention which is advantageous from production-engineering points of view is afforded if the pressure-measuring tube connecting device and the respiratory gas conduction device are of an integral construction.

In accordance with a particular aspect of the present invention the connecting, structural component is provided with a plate portion, wherein the respiratory gas conduction device passes through the plate portion. That plate portion preferably forms a labyrinth cover means coated with a sound-insulating soft material. That soft material advantageously acts at the same time as a sealing means between adjacent portions of the labyrinth.

A further embodiment of the invention which is advantageous from production-engineering points of view is afforded if both tube connecting projections extend substantially perpendicularly from the plate portion. The connecting structural component in that case can be in a particularly advantageous manner in the form of a plastic material injection molding with tube portions which are formed integrally, that is to say in one piece, on the plate portion.

The plate portion is advantageously provided with a sealing device for fitting the structural component on to a labyrinth casing in sealing relationship. A plug connecting device is advantageously provided for fixing the connecting structural component, in particular for fixing the structural component to a bottom structure of a CPAP-unit.

BRIEF DESCRIPTION OF THE DRAWINGS

Further details and features of the invention will be apparent from the description hereinafter of a preferred embodiment of the invention with reference to the drawing in which.

DETAILED DESCRIPTION OF PREFERRED EMBODIMENTS

Figure 1:
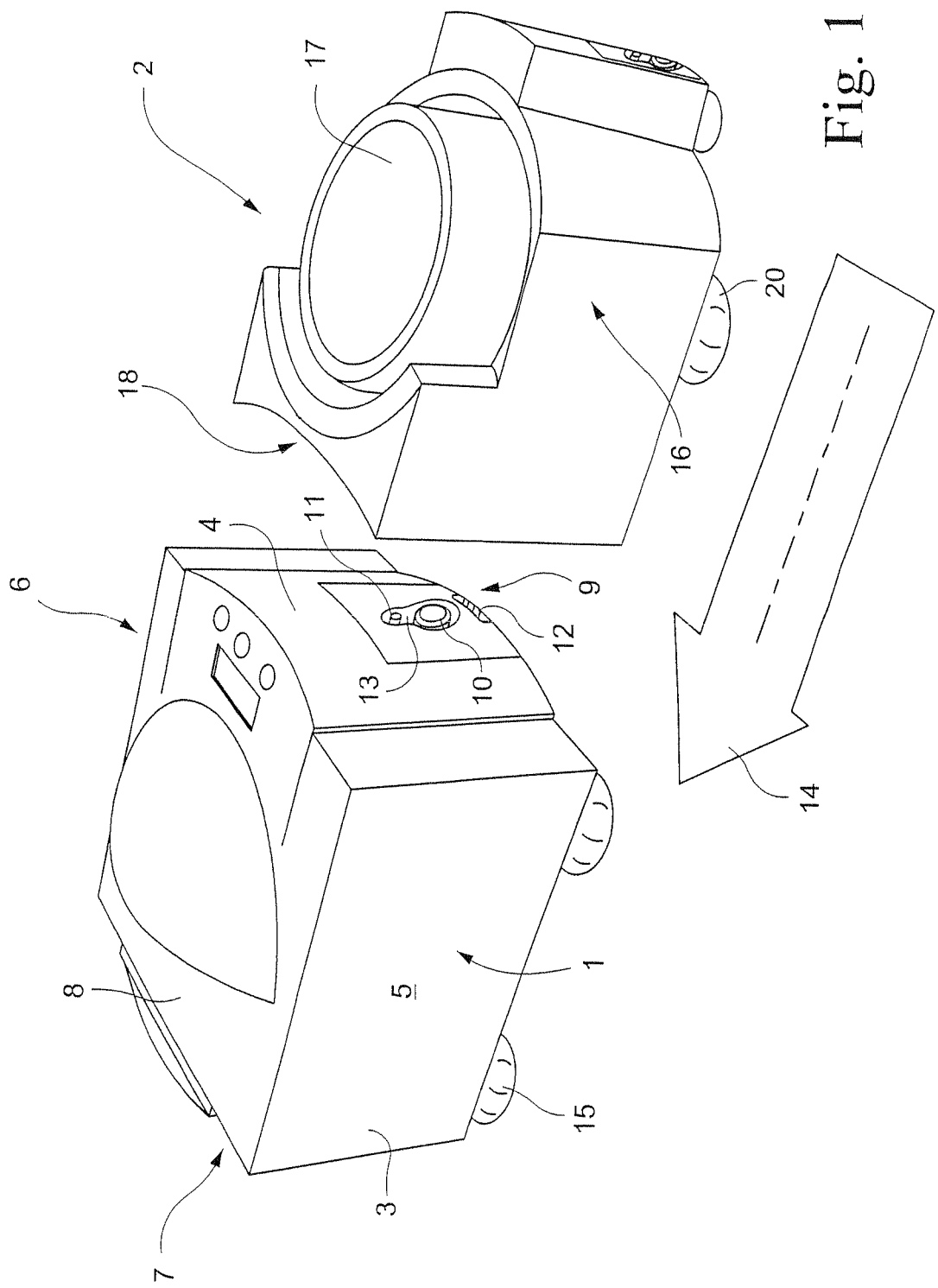
FIG. 1 shows an assembly comprising a CPAP-unit and a humidifying apparatus which can be laterally coupled directly to the front or end thereof.

The apparatus arrangement shown in FIG. 1 includes a CPAP-unit here generally identified by reference numeral 1 and a humidifying apparatus 2 which can be connected thereto in modular relationship. Here the CPAP-unit 1 has a substantially block-shaped or box-shaped housing 3 which has a front end face 4, two side faces 5, 6 which are arranged in pairs in mutually opposite relationship and which are in substantially parallel relationship with each other, and a rear side 7 which is arranged in the rearward region of the housing 3 in relation to the front end face 4, as well as an upper top face 8. Provided in the region of the front end face 4 is a connecting device 9 which, in the embodiment illustrated here, has a respiratory gas connecting portion 10, a pressure-measuring tube connecting portion 11 and an electrical connecting device 12. The respiratory gas connecting portion 10 and the pressure-measuring tube connecting portion 11 are arranged recessed substantially completely in an opening 13 which is only indicated here. The contact elements of an electrical connecting device 12 are also accommodated in an opening or recess so that those connecting members also do not project or do not project substantially beyond a surface defined by the front end face 4.

In the embodiment illustrated here the front end face 4 is of a slightly curved configuration, thereby affording particularly effective assistance in terms of centering the humidifying apparatus 2. The respiratory gas connecting portion 10 and the pressure-measuring tube connecting portion 11 are oriented in such a way that they extend substantially parallel to the joining direction which is indicated in simplified form by the arrow 14.

In its bottom region the CPAP-unit 1 has support or erection members (here support feet 15) which are such that the connecting members of the connecting device 9 are held at a predetermined vertical heightwise level which is matched precisely to the corresponding heightwise level of the connecting members of the humidifying apparatus 2.

The humidifying apparatus 2 includes a base body 16 and a liquid storage container 17 which is accommodated therein. The liquid storage container 17 can be removed from the base housing 16 for example for refilling it with humidifying liquid. The base housing has a connecting surface portion 18 which is of a correspondingly complementary configuration to the front end face 4 of the CPAP-unit 1 and in which are disposed the connecting members described in greater detail hereinafter with reference to FIG. 2.

On a side which is in opposite relationship to the connecting surface portion 18 the base housing 16 is again provided with connecting members which in terms of their structure and their arrangement substantially correspond to the connecting device 9 which has already been described with reference to the CPAP-unit 1. In that way it is then possible for the hose connecting plug provided for example for connection to the CPAP-unit 1 also to be connected directly to the humidifying apparatus 2. In that case connection of the pressure-measuring tube is achieved at the same time.

The humidifying apparatus 2 also has support feet 20 which provide that the connecting members on the humidifying apparatus in the region of the connecting surface portion 18 are held at a vertical heightwise level which corresponds to that of the connecting device 9.

Figure 2:
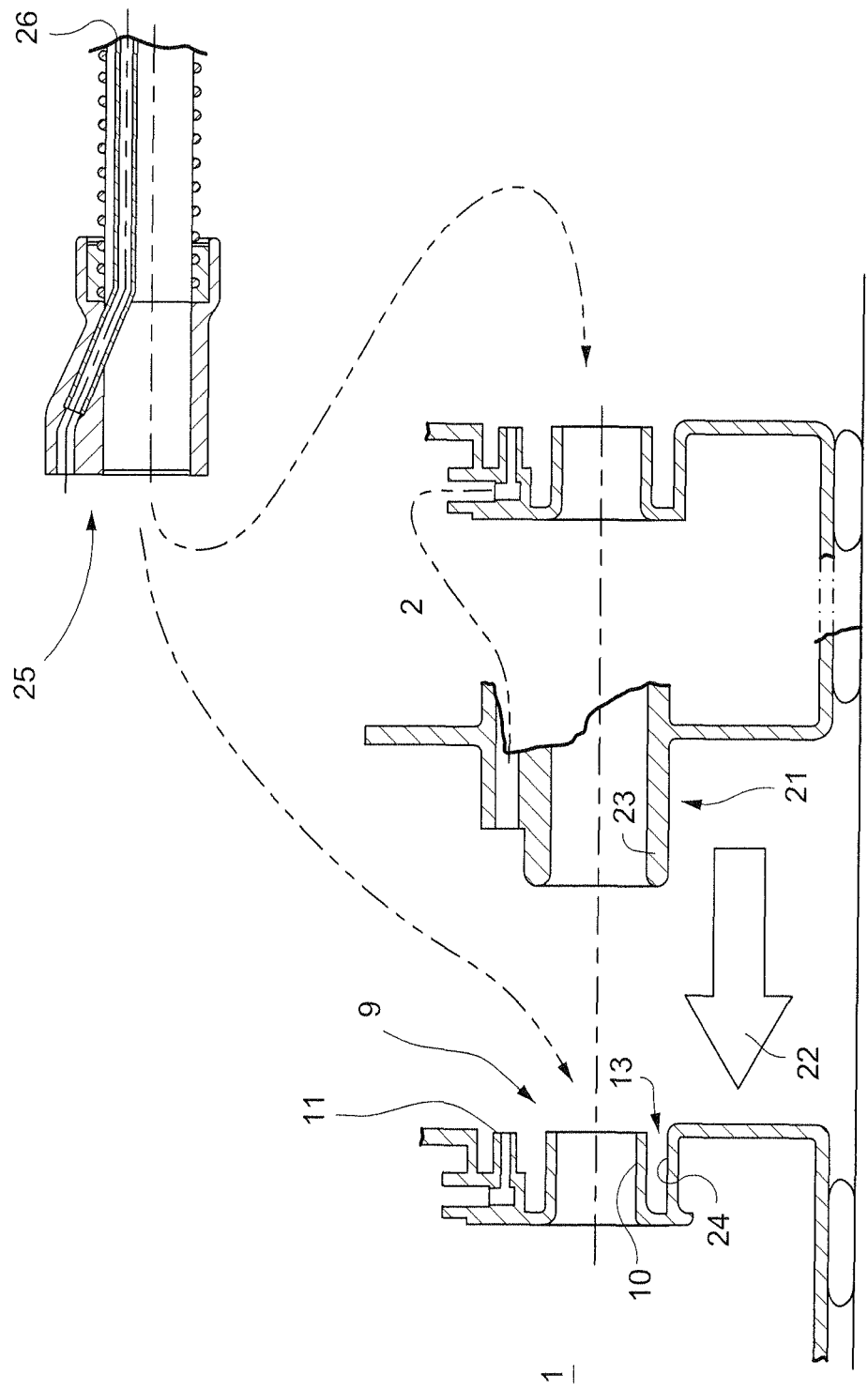
FIG. 2 is a simplified sectional view to explain the modular structure of the CPAP-assembly shown in FIG. 1.

As can be clearly seen from FIG. 2 the connecting device 9 on the CPAP-unit 1 is of a complementary configuration to the connecting device 21 on the humidifying apparatus 2. As indicated by the arrows 22 the two connecting devices 9 and 21 can be moved into the joined position in relation to each other. Particularly effective pre-positioning of the connecting members, in particular the respiratory gas connecting portion 10 and the corresponding counterpart portion 23, is achieved in this embodiment by the counterpart portion 23 also being centered by the inside wall 24 of the opening 13. The respiratory gas connecting portion 10 and the counterpart portion 23 on the humidifying apparatus 2 are disposed at exactly the same vertical heightwise level. Provided on the output side of the humidifying apparatus is a connecting structure which in terms of its essential dimensions corresponds to the connecting structure provided on the CPAP-unit. The respiration tube connecting plug 25 illustrated here can thus be coupled if required directly to the CPAP-unit 1 or to the humidifying apparatus 2. By virtue of a pressure-measuring connecting conduit which is indicated into the humidifying apparatus, a communication is afforded between the pressure-measuring tube 26 and the pressure-measuring tube connecting portion 11, when the respiration tube connecting plug 25 is connected to the humidifying apparatus 2. The CPAP-apparatus arrangement described hereinbefore with reference to FIGS. 1 and 2 can be used as described in the following example of use.

It is firstly assumed that the CPAP-unit 1 is already set up on a table top, and now the respiratory gas being conveyed by the CPAP-unit 1 is to be humidified.

For that purpose, as indicated in FIG. 1, the humidifying apparatus according to the invention is also set up on the table top and is fitted on to the CPAP-unit in a joining direction which is parallel to the surface of the table and substantially perpendicular to the front end face of the CPAP-unit 1. When that is done, the connecting devices 9 and 21 which are provided on the CPAP-unit 1 and the humidifying apparatus 2 come together in the joining position. In addition, a voltage supply to a heating device provided on the humidifying apparatus 1 is also afforded by way of an electrical connecting device 12 which is only shown in FIG. 1. As soon as the two connecting devices 9, 21 have moved completely into the joined position, the two modules are fixed in that joined position by a latching device (not shown) so that the humidifying apparatus 2 is reliably coupled to the CPAP-unit. The respiratory gas tube which is originally connected directly to the CPAP-unit 1 and which has an integrated pressure-measuring conduit can be connected directly to the humidifying apparatus by way of the respiratory gas connecting plug identified by reference numeral 25 in FIG. 2. That also affords a corresponding coupling between the pressure-measuring tube 26 and the pressure-measuring tube connecting portion 11 provided on the CPAP-unit 1.

For the purposes of introducing humidifying water into the liquid storage container 17, the latter is removed from the base housing 16 of the humidifying apparatus. After the liquid storage container is filled it can be fitted into the base housing 16 again. The CPAP-apparatus system formed from two modules which can be laterally coupled, with a refilling unit which can be removed cartridge-like, is now ready for operation.

Figure 3:
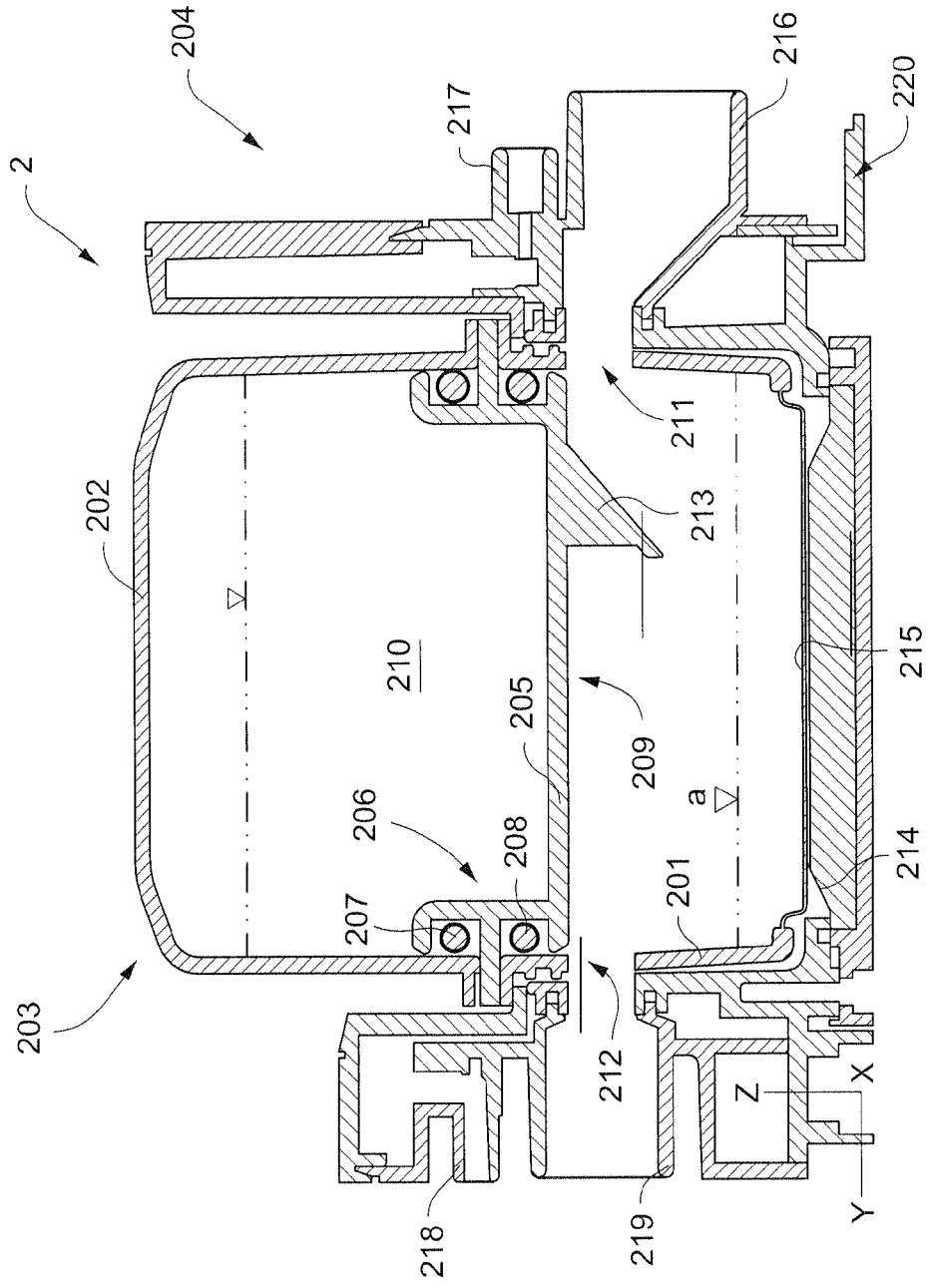
FIG. 3 is a simplified view in longitudinal section through a humidifying apparatus according to the invention.

The view in FIG. 3 shows a longitudinal section through an apparatus for humidifying a respiratory gas (referred to hereinafter as the humidifying apparatus), in accordance with a preferred embodiment of the invention. Here, the illustrated embodiment of the humidifying apparatus includes a refilling unit 203 which is formed from a trough element 201 and a cup portion 202 coupled thereto and which can be easily removed from a support or installation housing 204 which here is of a multi-part nature.

The trough element 201 and the cup portion 202 are coupled together in sealing relationship. The trough element 201 and the cup portion 202 are coupled by way of a sealing structure 206 which, in the embodiment illustrated here, has a first sealing ring 207 and a second sealing ring 208. The two sealing rings 207 and 208 are accommodated in peripheral grooves provided in a separating element 209. The separating element 209 has a separating wall 205 which is here of an integral nature. The separating wall 205 separates the internal region of the cup portion 202 from the internal region of the trough element 201.

Formed in the cup portion 202, in conjunction with the separating wall 205, is a liquid storage space 210 in which initially the predominant part of the liquid provided for humidifying the respiratory gas is stored. Formed in the trough element 201 arranged beneath the cup portion 202 is a separate humidifying region in which only a partial amount of the humidifying liquid is accommodated. The level a of the liquid accommodated in the trough element 201 is maintained at a predetermined filling height by way of a quantitative control device. In the course of gradual consumption of the fluid in the trough element 201, fluid is supplied as a make-up flow successively or continuously from the liquid storage space 210. A preferred embodiment of a quantitative control device which is provided for that purpose will be described in detail hereinafter with reference to FIG. 3.

Here the trough element 201 is of a substantially shell-like nature and has a respiratory gas feed opening 211 and a respiratory gas discharge opening 212. The respiratory gas which is conveyed by a CPAP-unit (not shown here) can flow into the trough element 201 by way of the respiratory gas feed opening 211, according to the respiration activity of a patient. By means of a direction-changing device 213 which is only shown here in simplified form the feed flow of respiratory gas is directed on to the liquid in the trough element 201. In that situation the respiratory gas supplied thereto is enriched with moisture. The correspondingly humidified respiratory gas can then flow away, by way of the respiratory gas discharge opening 212.

In the embodiment illustrated here the trough element 201 can be heated by means of a heating device 214. The heating device 214 comprises a heating element which is arranged in the support housing 204 in such a way that the bottom region of the trough element 201 can come into intimate contact therewith. In order to increase the transmission of heat between the fluid in the trough element 201 and the heating device 214 the bottom region 215 of the trough element 201 is formed from a material of high thermal conductivity, for example metal. In the last-mentioned embodiment the above-mentioned bottom region 215 can be formed for example by the insert molding method in the actual main body of the trough element 201. The trough element 201 is of such a configuration that it can be inserted as an easy fit in self-positioning relationship into the support housing 204. In that case the respiratory gas feed opening 211 and the respiratory gas discharge opening are aligned with conduits or openings provided in correspondingly complementary manner in the support housing 204.

In the region adjacent to the respiratory gas feed opening 211 the support housing 204 is provided with a connecting portion 216 which, in the embodiment illustrated here, can be fitted directly on to a connecting portion of a CPAP-unit, which is of a correspondingly complementary configuration. Provided in the immediate proximity of the connecting portion 216 is a further connecting portion 217 which can be coupled to a pressure-detecting connection provided on a CPAP-unit. The connecting portion 217 forms part of a conduit system which ultimately communicates with the pressure-measuring connecting portion 218 provided on an opposite side of the humidifying apparatus. In particular a pressure-measuring tube can be connected to that pressure-measuring connection 218 for detecting the pressure in the region of the respiration hose, a gas change valve or possibly also directly in the mask region.

Beneath the pressure-measuring connecting portion 218 the support housing 204 is provided with a respiration tube connecting portion 219. The tube connecting members formed at the outlet side on the humidifying apparatus are identical to that of a CPAP-unit, in such a way that corresponding connecting tubes or hoses can be optionally connected either directly to the CPAP-unit or if necessary, when using the humidifying apparatus, only to the outlet side of the humidifying apparatus 2. Provided beneath the connecting portion identified by reference numeral 216 is a plug connecting device (not shown here) by way of which it is possible to make an electrical connection between the heating device 214 and a voltage supply device provided on the CPAP-unit. Optionally it is also possible for electrical signals, for example pressure-measuring signals, to be transmitted by way of that plug connecting device.

The support housing 204 is further provided with a fixing device 220, by way of which the humidifying apparatus can be mechanically comparatively rigidly coupled to a CPAP-unit.

A preferred embodiment of a quantitative control device for quantitative metering of the amount of fluid in the trough element 201 will be described hereinafter with reference to FIG. 4. The liquid storage space 210 and the humidifying region formed in the trough element 201 are separated from each other by way of the separating wall 205. The fluid stored in the liquid storage space 210 can be passed if required into the humidifying region by way of a fluid conduit device 221. In this case control of the make-up flow of fluid is implemented by control of the make-up introduction of air into the liquid storage space. In the embodiment illustrated here regulation of the make-up introduction of air is effected by way of a quantitative control conduit device 222 which, similarly to the above-mentioned fluid conduit device 221, passes vertically through the separating wall 205. The quantitative control conduit device 222 has a first mouth opening 223 and a second mouth opening 224. The first mouth opening 223 is arranged at the height of the desired or reference level a. As long as the first mouth opening 223 is closed by the fluid in the trough element 201, no make-up flow of air can pass into the liquid storage space 210 so that in turn no fluid can flow away out of the liquid storage space 210 by way of the fluid conduit device 221. As soon as the level a falls below the level of the first mouth opening, a make-up flow of air can pass into the liquid storage space, whereby in turn fluid can pass out of the liquid storage space 210 into the trough element 201 or the separate humidifying region formed therein. The fluid conduit device 221 has a discharge mouth opening 225 which is somewhat below the reference level identified here by the letters a.

In the embodiment illustrated here the fluid conduit device 221, the quantitative control conduit device 222 and the separating wall 205 are formed by an integral member. For the purposes of introducing the liquid into the liquid storage space, it is possible for that integral member to be withdrawn from the cup portion 202. The cup portion 202 can optionally also be provided with a corresponding refilling opening which can be sealingly closed. The cup portion 202, the integral member having the separating wall and the trough element can each be cleaned separately. The quantitative control conduit device 222 is of such a design configuration that the second mouth opening 224 provided thereon is above the maximum filling level of the liquid storage space 210.

Figure 4:
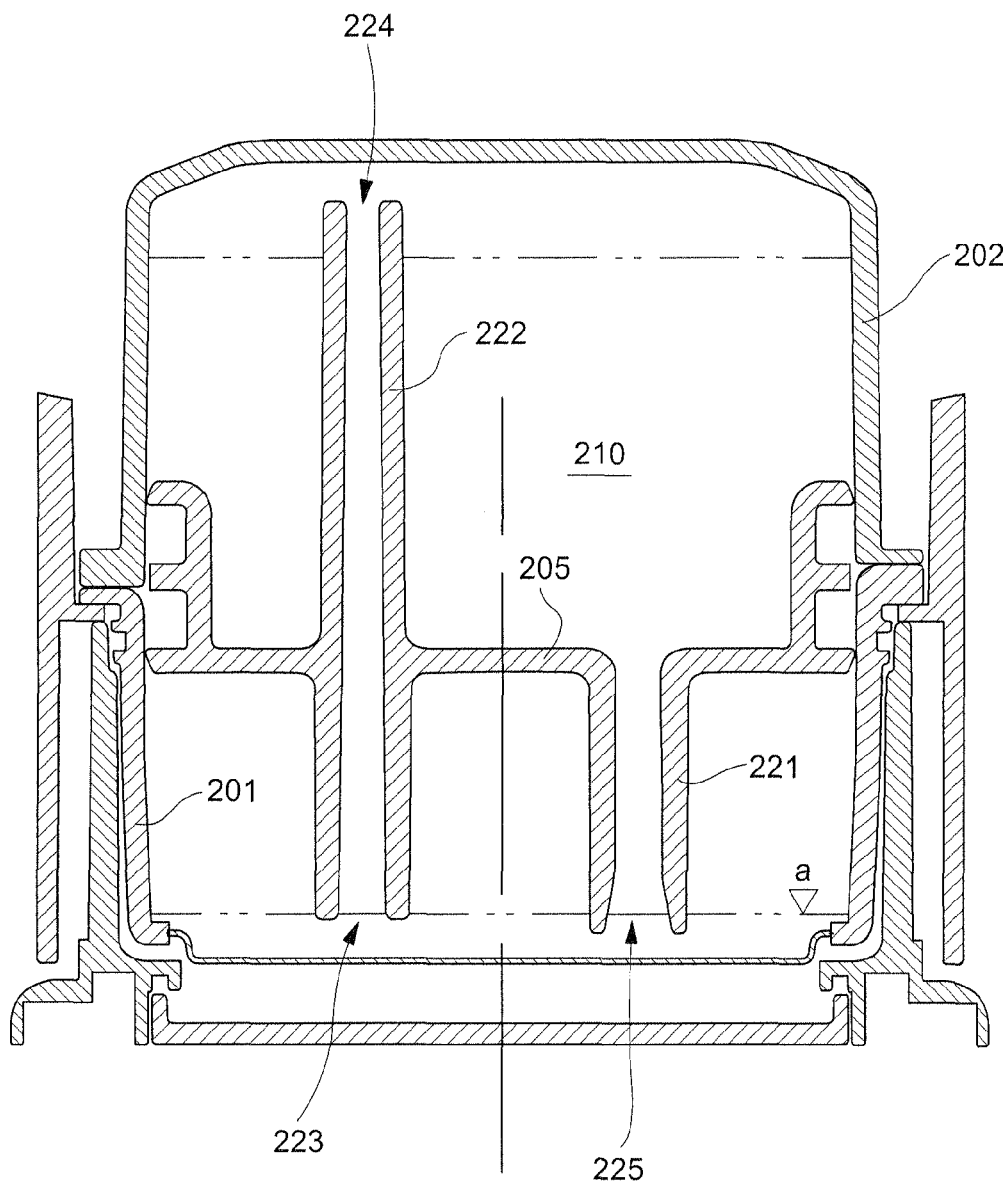
FIG. 4 is a simplified view in section taken perpendicular to the section line A-A in FIG. 3.
Figure 5:
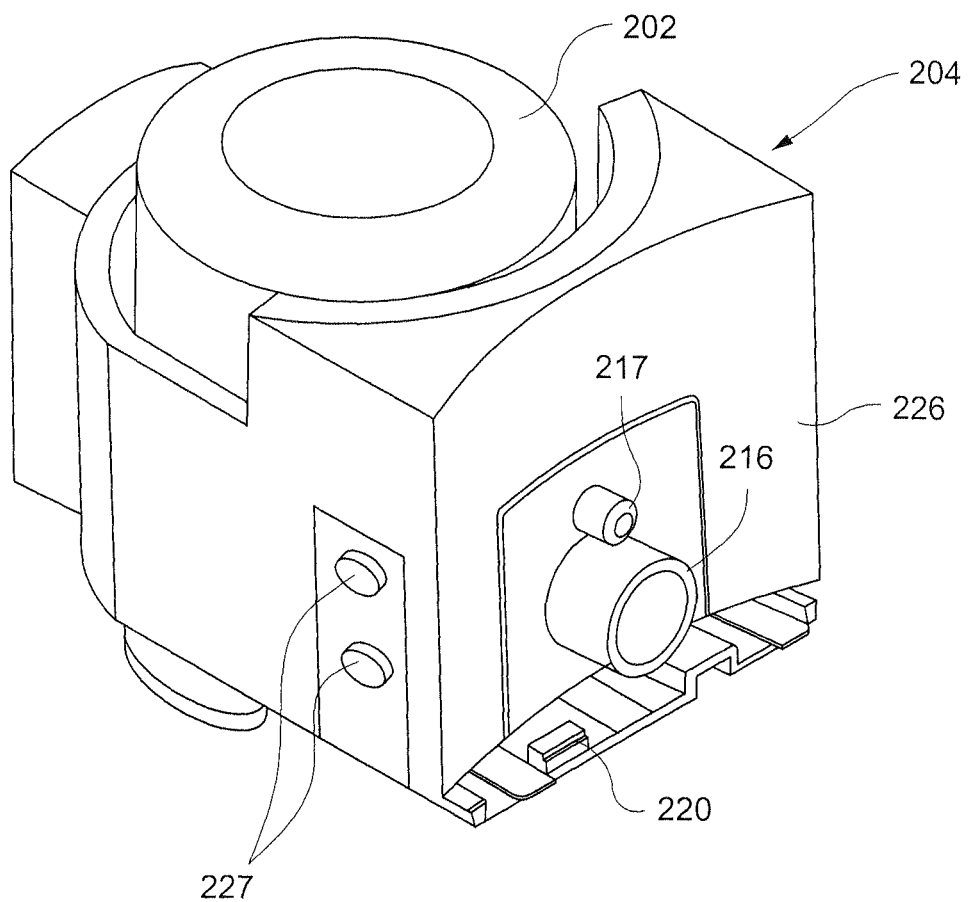
FIG. 5 is a perspective view of the humidifying apparatus of FIGS. 3 and 4 viewing on to the plug connecting arrangements provided for connection to a CPAP-unit.

FIG. 5 is a perspective view of the humidifying apparatus described hereinbefore with reference to FIGS. 3 and 4. The cup portion which is preferably formed from a transparent material can be seen here in the form of a bowl of substantially cylindrical configuration. That bowl is fitted in a receiving portion which is also cylindrical and which is formed in the support housing 204. In the region of the cup portion 202 the support housing 204 is of such a design configuration that the cup portion can be gripped with one hand. The connecting portion 217 and the pressure-measuring connecting portion 218 which have already been described with reference to FIG. 3 are provided in the region of the rear side 226 of the humidifying apparatus. Provided beneath those connecting portions is the fixing device which is identified by reference 220 in FIG. 3 and which can provide particularly rigid coupling of the humidifying apparatus to a corresponding CPAP-unit. Provided in a receiving recess beneath the connecting portion 216 is an electrical plug connecting arrangement (not shown here) for providing an electrical connection for the heating device to the associated CPAP-unit.

Provided in the lateral region of the outer housing are switch members 227, by way of which it is possible to set on the one hand the temperature of the liquid in the trough element 201 and the switch-on time for the humidifying apparatus.

The rear side 226 of the humidifying apparatus is of a configuration corresponding to the front side of a CPAP-unit described hereinafter with reference to FIG. 6a so that the humidifying apparatus can be connected in a modular manner virtually without any intermediate space to the CPAP-unit.

Figure 6A:
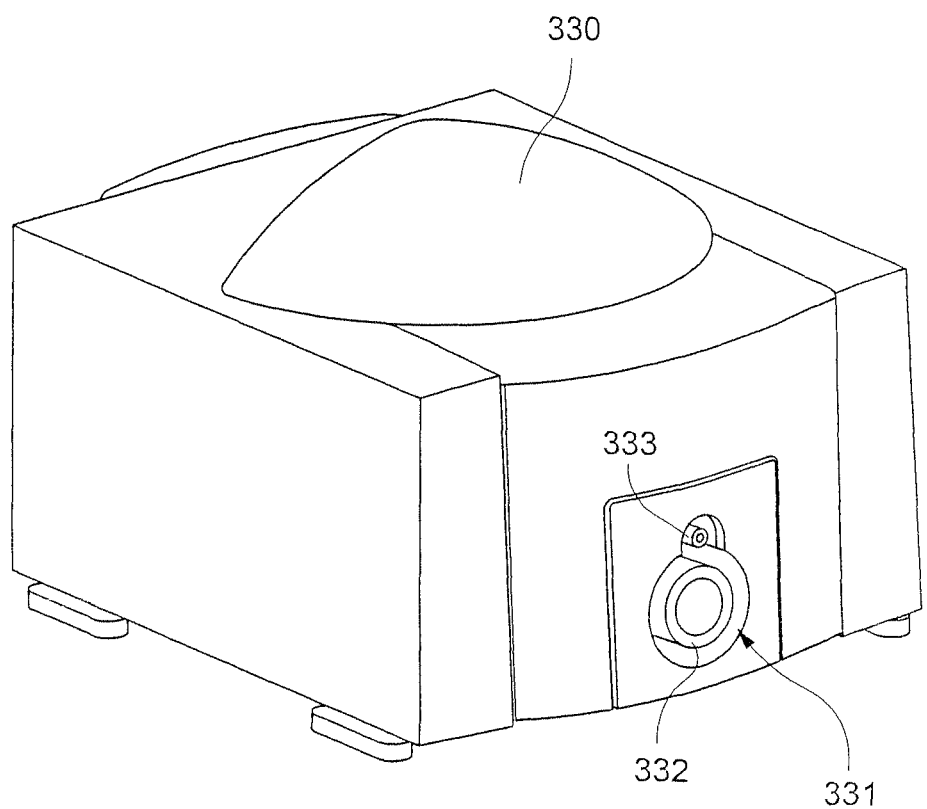
FIG. 6a is a perspective view of a CPAP-unit with a connecting structure which is complementary to the humidifying apparatus.

The CPAP-unit shown in FIG. 6a has a substantially cuboidal housing, in the upper region of which is provided a gripping arrangement 330, by way of which the CPAP-unit can be gripped in an ergonomically advantageous manner. Provided in a front end region are connecting members 331, for the connection of at least one respiration tube or hose.

The illustrated embodiment has a respiration hose connecting projection 332 and a pressure-measuring tube connecting projection 333. The arrangement of those connecting members substantially corresponds to the arrangement of the connecting members 216 and 217 described with reference to FIG. 3. The connecting members 231 are further of such a configuration that the connecting members 216, 217 on the humidifying apparatus (FIG. 3) can be directly fitted on or fitted in. Also provided in the bottom region of the CPAP-unit are engagement structures which can be brought into engagement with engagement portions of a complementary configuration, on the humidifying apparatus. The connecting members 331 are here arranged in recessed relationship in such a way that they do not project beyond an outside surface and in particular a front surface of the housing.

Figure 6B:
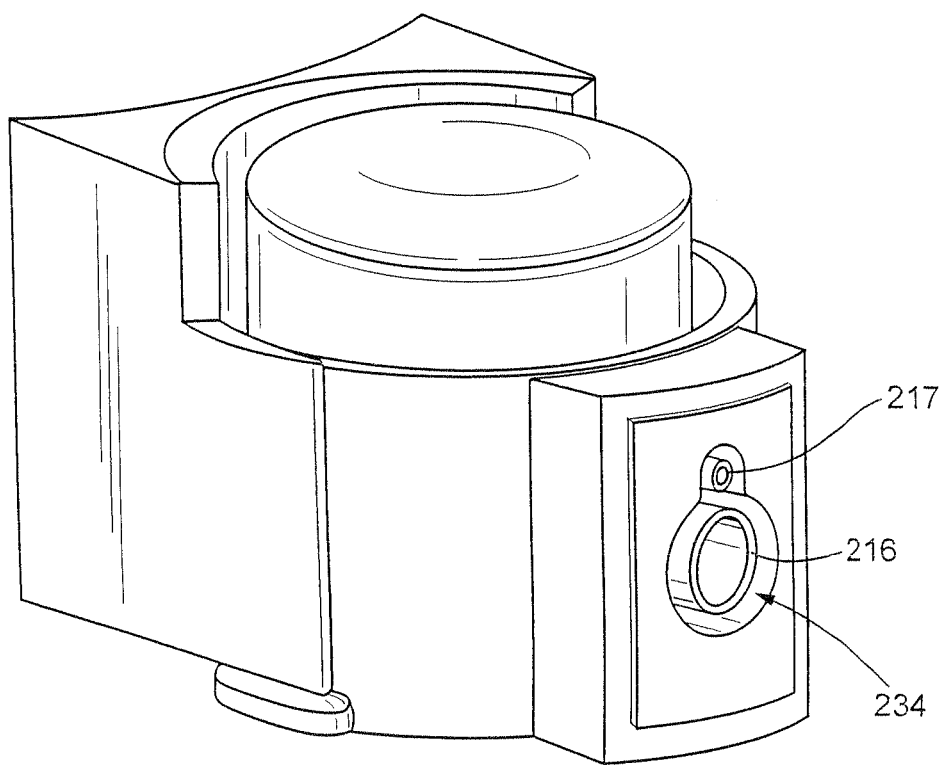
FIG. 6b shows a perspective view of the humidifying apparatus of FIG. 5 but viewing on to the connecting structures at the respiration tube side.

FIG. 6b shows the humidifying apparatus described hereinbefore with reference to FIGS. 3, 4 and 5, viewing on to the front region thereof. The connecting portions 216 and 217 are arranged in recessed relationship, similarly as also in regard to the CPAP-unit. The connecting portions are surrounded by a plug-receiving space 234 into which can be inserted a plug preferably formed from a soft material, in particular silicone rubber.

The plug-receiving space 234 is preferably of such a nature that a corresponding plug slides both on the respective projection 216, 217 and also along the wall of the plug-receiving space 234.

The invention is not limited to the embodiments by way of example described hereinbefore. For example it is also possible for the described humidifying apparatus to be integrated directly into a corresponding CPAP-unit. It is also possible to fit into the support housing which can be docked in a simple fashion to a CPAP-unit, refilling units which deviate in respect of their structure and the humidifying principle involved, from the described humidifying apparatus. It is also possible for the trough element of the humidifying unit to be so designed that it can be connected directly to the CPAP-unit, omitting the support or installation housing. The described humidifying apparatus can also be connected to a respiratory gas source, with the interposition of a hose conduit. The refilling unit can also be arranged in the form of a substantially trough-like unit under the CPAP-unit.

Figure 7:
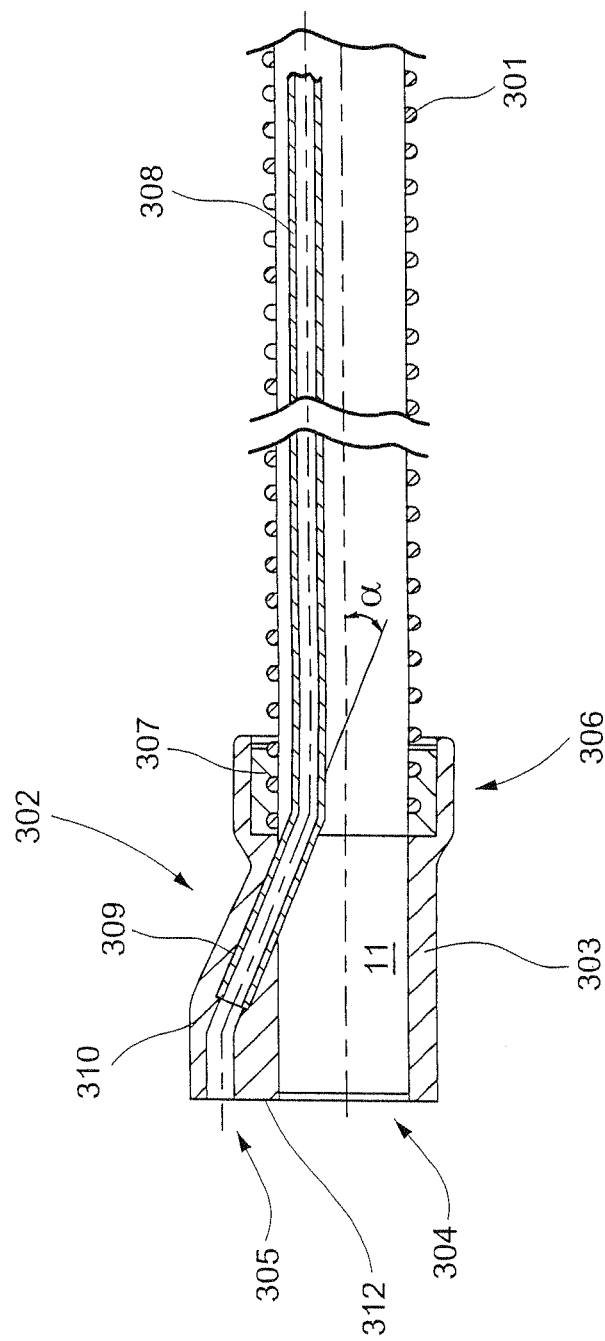
FIG. 7 is a simplified view in axial section through an end portion of a respiration tube and associated connecting device.

The respiration tube or hose 301 shown in FIG. 7 is provided in its end region with a connecting device 302 which here has a base body 303 formed from an elastomer material, in particular silicone rubber, with two coupling portions 304, 305 formed therein.

The two coupling portions 304, 305 are formed integrally by mutually parallel tube zones which are of circular cross-section. The inside diameter of the respective tube zone is slightly smaller than the outside diameter of the connecting projections which pass into the two tube zones when the plug is connected thereto and in that case is slightly enlarged.

Formed in the region of the base body, which is towards the hose or tube, is a fixing portion 306 in which the respiration tube 301 is fixed by way of a ring element 307. The ring element 307 is here also formed from an elastomer material and is secured by adhesive to the outside surface of the respiration tube.

An additional tube—here a pressure-measuring tube 308—is guided in the interior of the respiration tube 301. The pressure-measuring tube 308 opens into the coupling portion 305 by way of a passage duct 309 formed in the base body 303. The pressure-measuring tube 308 is secured by adhesive or vulcanisation in the base body 303. The passage duct 309 is of such a configuration that the pressure-measuring tube 308 is only slightly curved. The angle α between the longitudinal center line of the coupling portion 304 and the longitudinal center line of the passage duct 309 is preferably less than 35°.

The transition of the inside wall of the pressure-measuring tube 309 into the coupling portion 305 is effected here substantially steplessly. A corresponding shoulder 310 is provided at the end of the passage duct 309, for that purpose.

The respiratory gas conduit region 311 formed in the base body 303 in this case also forms a substantially stepless transition into the inner region of the respiration tube 301.

With suitable elasticity of the tubes 301, 308, it is possible for them to be passed to the end face 312 of the base body 303 so that the coupling members on the unit side can pass directly into the tubes 301, 308.

Figure 8:
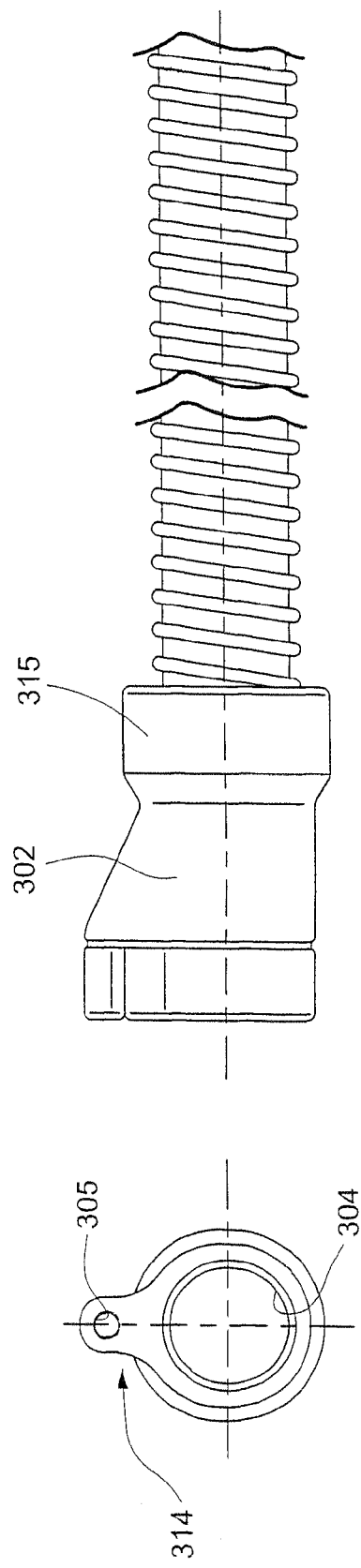
FIG. 8a is a front view of the base body of the connecting device.
FIG. 8b is a side view of the respiration tube with connecting device mounted thereto.

The external configuration of the base body shown in FIG. 7 will be described in still greater detail with reference to FIGS. 8a and 8b. As can be clearly seen in particular from FIG. 8a, the coupling portion intended for the connection of the additional tube is arranged at a radial spacing from the respiratory gas conduit coupling portion 304 in a region 314 of the base body 303, which projects radially outwardly in a nose-like configuration. That provides for effective preliminary positioning of the base body in a recess provided in the unit.

That region which extends radially outwardly in a nose-like configuration decreases continuously towards the end of the base body 1, which is towards the respiration tube. Provided in the region of the end towards the tube is a peripheral bead or ridge 315, by way of which a flow of forces between the hose and the plug structure, which is advantageous from mechanical points of view, is achieved.

Figure 9:
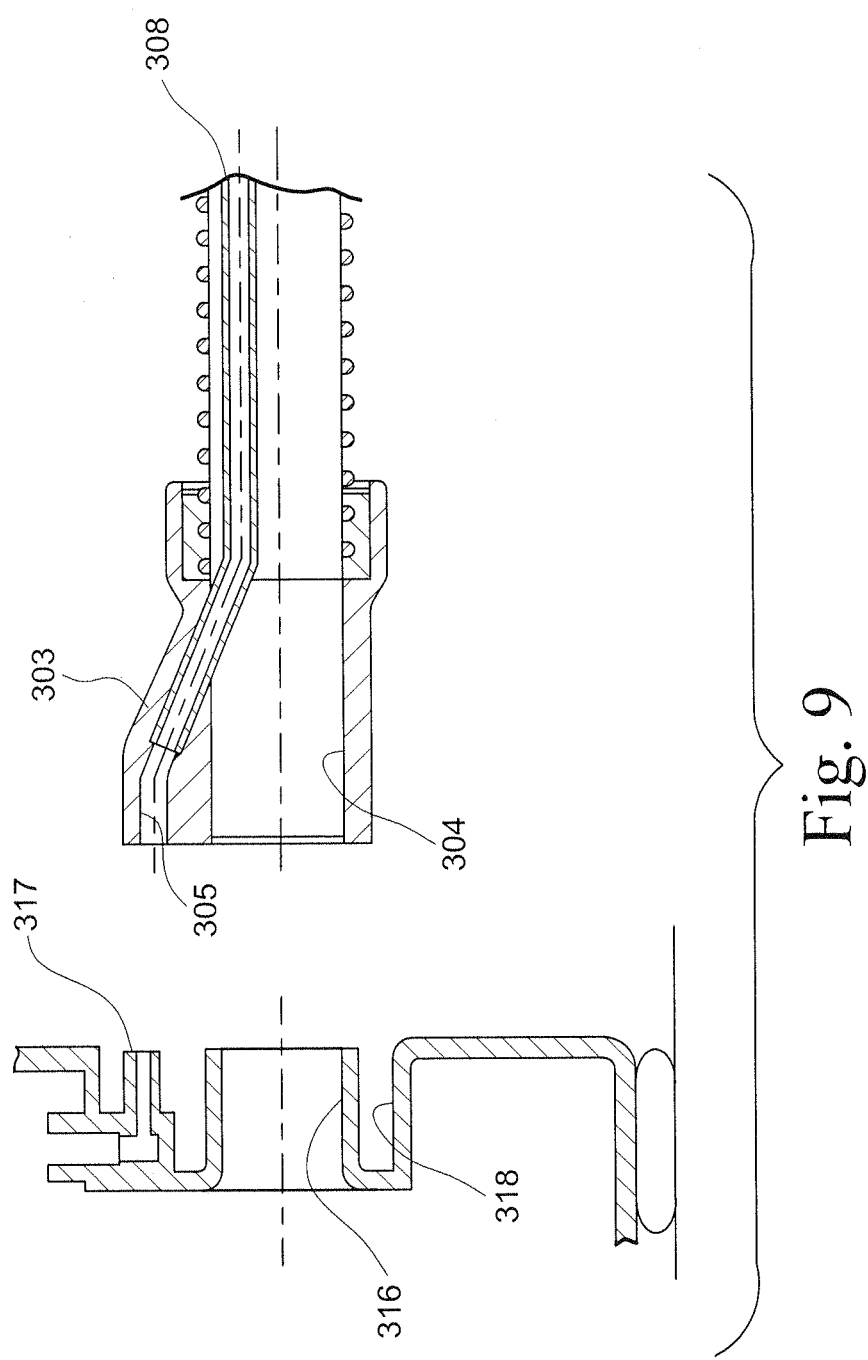
FIG. 9 is a simplified view in section to illustrate a suitable complementary connecting structure on the unit.

FIG. 9, for explanatory purposes, shows a preferred embodiment of a connecting structure on the unit, which connecting structure is of a substantially complementary configuration to the coupling portions 304, 305 provided in the base body 303 of the plug.

The projection portion which is identified here by reference 316 passes into the coupling portion 304 in the joined position of the assembly. The projection portion identified by reference numeral 317 comes into engagement with the coupling portion in the joined position. The two projection portions 316, 317 are arranged in recessed relationship in a recess 318. The inside wall which defines the recess 318, in conjunction with the external contour of the base body 303 shown in FIG. 8a, provides for pre-positioning thereof.

Figure 10:
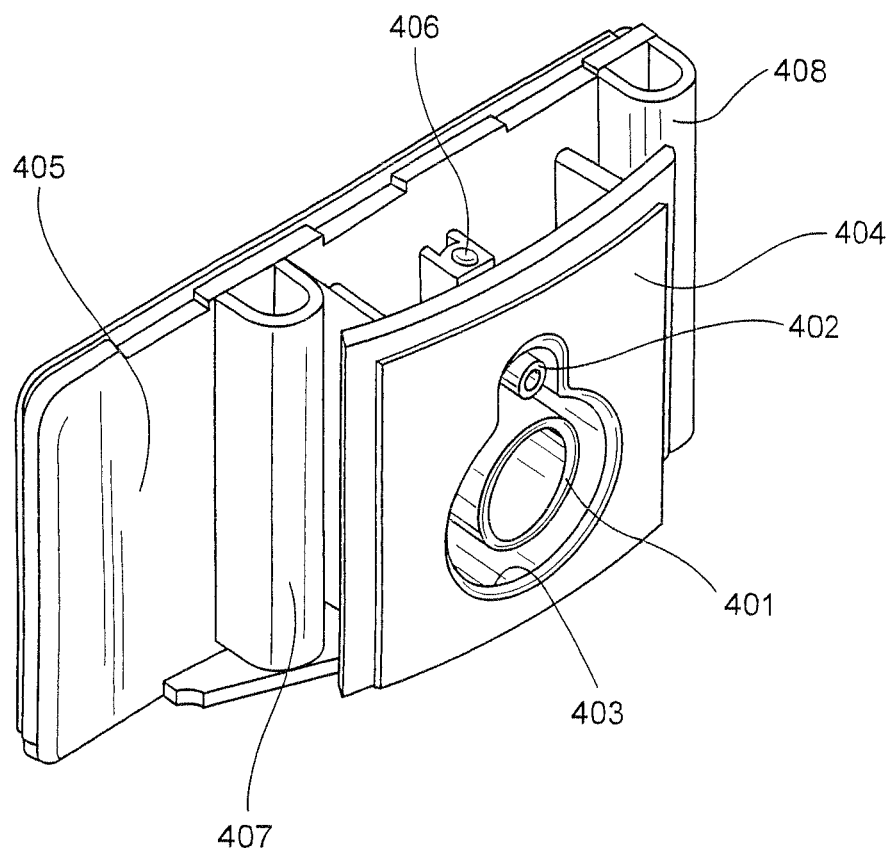
FIG. 10 shows a perspective view of a structural component in accordance with a preferred embodiment of the invention, and FIG. 11a, b, c show three different compatible connecting options.

The connecting structural component shown in FIG. 10 includes a respiratory gas conduction device which is here in the form of a tube projection portion 401. A further tube projection portion 402 is arranged adjacent to that tube projection portion 401, leaving an intermediate space. The tube projection portion 402 forms a pressure-measuring tube connecting device. The two tube projection portions 401, 402 are arranged in recessed relationship in a recess 403. That recess is surrounded by a front cover plate 404. The cover plate 404 and the wall defining the recess 403 are formed in one piece.

In a region remote from the end of the tube projection 401, which is towards the tube, it opens into a base plate 405 which here forms a cover plate for a labyrinth arrangement. This labyrinth arrangement which is not described in greater detail here forms a prolonged respiratory gas guide path for the absorption of any odors produced by a blowing device. The base plate 405 is coated with a sound-absorbing material, in particular foam, on the rear side which is not visible here.

Provided in a region between the base plate 405 and the cover plate 404 is a connecting duct 406, by way of which the interior of the tube projection 402 can be coupled to a pressure transducer arranged on a control board.

The connecting structural component is further provided with fixing devices 407, 408, by way of which that component can be fixed in a CPAP-unit in an easily interchangeable manner.

Figure 11A:
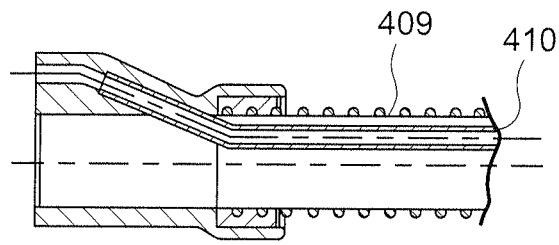
Figure 11B:
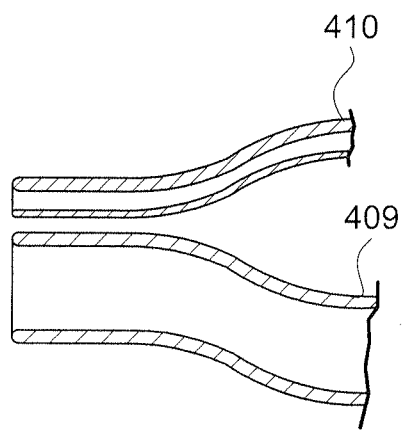
Figure 11C:
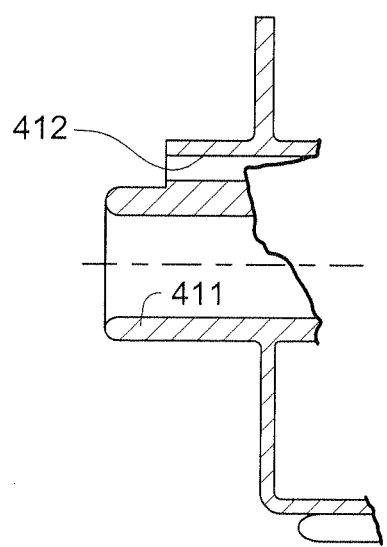

More particularly but not exclusively the conduit devices shown in FIGS. 11a, 11b and 11c can be connected to the illustrated connecting structural component.

In this respect FIG. 11a shows a compact plug which is advantageous in terms of handling, from ergonomic points of view, with an integrated pressure-measuring tube passage configuration.

FIG. 11b shows a respiration tube 409 and a pressure-measuring tube 410 which is independent thereof, both of which can be connected without a plug arrangement directly to a corresponding CPAP-unit, by way of the connecting structural component according to the invention.

FIG. 11c is a greatly simplified view showing a coupling portion of a humidifying apparatus which can be fitted directly to a CPAP-unit by way of the structural component according to the invention. In that case the projection portion identified by reference numeral 411 engages with the tube projection 401 and the bore portion 412 with the tube projection 402.

The invention claimed is:

1. An apparatus for supplying a respiratory gas to a patient, comprising:
a CPAP unit configured to generate a flow of respiratory gas;
a humidifying apparatus adapted to be coupled to the CPAP unit and humidify the flow of respiratory gas; and
a respiration tube adapted to be coupled to the CPAP unit or the humidifying apparatus and configured to deliver the flow of respiratory gas to the patient, wherein
the CPAP unit comprises a respiratory gas connection portion on a side of the CPAP unit that is configured to be coupled to the respiration tube or the humidifying apparatus to deliver the flow of respiratory gas to the respiration tube or the humidifying apparatus, respectively,
the humidifying apparatus comprises a connection portion on a side thereof that is configured to connect to the respiratory gas connection portion of the CPAP unit, a longitudinal axis of the connection portion being provided at an exact same vertical heightwise level on the side of the humidifying apparatus as a longitudinal axis of the respiratory gas connection portion is provided on the side of the CPAP unit, such that the connection portion of the humidifying apparatus and the respiratory gas connection portion of the CPAP unit are joined when the humidifying apparatus and the CPAP unit are moved laterally towards each other while placed on a common flat surface, the humidifying apparatus comprising a fixing device to rigidly couple the humidifying apparatus to the CPAP unit,
the humidifying apparatus also comprises a respiration tube connection portion configured to connect the respiration tube to the humidifying apparatus, the respiration tube connection portion of the humidifying apparatus and the respiratory gas connection portion of the CPAP unit having respiration tube connecting members shaped to permit the respiration tube to be connected to either the CPAP unit or the humidifying apparatus,
the humidifying apparatus further comprises a housing, a heating element provided in a bottom portion of the housing, and a liquid storage container configured to store a supply of liquid to humidify the respiratory gas flow, the liquid storage container being configured to be inserted and removed from the housing in a cartridge-like manner and to be in contact with the heating element when inserted into the housing, and
the CPAP unit also comprises an electric terminal configured to receive an electric plug of the humidifying apparatus to electrically couple the CPAP unit and the humidifying apparatus, the electrical terminal being located in a recess of the CPAP unit below the respiratory gas connection portion so that the electric terminal does not extend beyond a surface defined by the side of the CPAP unit.

2. An apparatus according to claim 1, wherein a bottom region of the liquid storage container configured to contact the heating element comprises metal.

3. An apparatus according to claim 2, wherein the liquid storage container comprises a) a bottom portion including the bottom region, b) a top portion connected to the bottom portion, and c) a seal provided between the bottom portion and the top portion.

4. An apparatus according to claim 3, wherein the bottom portion of the liquid storage container comprises a respiratory gas feed opening configured to receive the flow of respiratory gas from the respiratory gas connection portion of the CPAP unit when the respiratory gas connection portion of the CPAP unit is connected to the connection portion of the humidifying apparatus.

5. An apparatus according to claim 4, wherein the respiratory gas feed opening of the bottom portion of the liquid storage container is configured to deliver the respiratory gas flow to a surface of a liquid stored in the liquid storage container.

6. An apparatus according to claim 5, wherein the bottom portion of the liquid storage container further comprises a direction-changing device configured to change a direction of the respiratory gas flow from the respiratory gas feed opening towards the surface of the liquid stored in the liquid storage container.

7. An apparatus according to claim 1, wherein the respiratory gas connection portion at the CPAP unit and the connection portion of the humidifying apparatus are correspondingly complementary shaped.

8. An apparatus according to claim 1, wherein the humidifying apparatus is adapted to be removably coupled to the CPAP unit.

9. An apparatus according to claim 8, further comprising a detaching device to detach the humidifying apparatus from the CPAP unit.

10. A method according to claim 9, further comprising coupling the side face of the CPAP unit to the side face of the humidifying apparatus at a different location from a location at which the respiratory gas connection portion and the connection portion of the humidifying apparatus are joined when the CPAP unit and the humidifying apparatus are moved laterally with respect to each other to bring the side faces of the CPAP unit and the humidifying apparatus into engagement.

11. A method according to claim 10, wherein the CPAP unit is coupled to the humidifying apparatus when a CPAP coupling device on the side face of the CPAP unit interlocks with a humidifying apparatus coupling device on the side face of the humidifying device, at least a portion of the CPAP coupling device being located away from the respiratory gas connection portion and at least a portion of the humidifying apparatus coupling device being located away from the connection portion.

12. A method of supplying a respiratory gas to a patient, comprising:
   fluidly and electrically connecting a CPAP unit and a humidifying apparatus by moving the CPAP unit and the humidifying apparatus laterally with respect to each other so that a side face of the CPAP unit engages a corresponding side face of the humidifying apparatus;
   generating a flow of respiratory gas with the CPAP unit; and
   humidifying the flow of respiratory gas with the humidifying apparatus,
   wherein the CPAP unit comprises a respiratory gas connection portion on the side face of the CPAP unit, and
   wherein the humidifying apparatus comprises a connection portion on the side face that is configured to connect to the respiratory gas connection portion of the CPAP unit, a longitudinal axis of the connection portion being provided at an exact same vertical heightwise level on the humidifying apparatus as a longitudinal axis of the respiratory gas connection portion is provided on the CPAP unit when the CPAP unit and the humidifying apparatus are placed on a common flat surface such that the connection portion of the humidifying apparatus and the respiratory gas connection portion of the CPAP unit are joined when the CPAP unit and the humidifying apparatus are moved laterally with respect to each other to bring the side faces of the CPAP unit and the humidifying apparatus into engagement with each other.

13. A method according to claim 12, further comprising:
   removably fixing the humidifying apparatus to the CPAP unit.

14. A method according to claim 13, wherein electrically connecting the CPAP unit and the humidifying apparatus comprises:
   electrically coupling a plug of the humidifying apparatus with an electric terminal of the CPAP unit configured to receive the plug of the humidifying apparatus, the electrical terminal being located in a recess of the CPAP unit below the respiratory gas connection portion so that the electric terminal does not extend beyond a surface defined by the side of the CPAP unit.

15. A method according to claim 14, wherein the humidifying apparatus further comprises a housing, a heating element provided in a bottom portion of the housing, and a liquid storage container configured to store a supply of liquid to humidify the respiratory gas flow, wherein the method further comprises:
   inserting the liquid storage container into the housing in a cartridge-like manner to be in contact with the heating element.

16. A method according to claim 15, wherein inserting the liquid storage container into the housing comprises inserting the liquid storage container in a direction perpendicular to the lateral coupling direction of the CPAP unit and the humidifying apparatus.

17. A method according to claim 16, wherein the liquid storage container comprises a bottom portion comprising a respiratory gas feed opening configured to communicate with the respiratory gas connection portion of the CPAP unit when the respiratory gas connection portion of the CPAP unit is connected to the connection portion of the humidifying apparatus, the method further comprising:
   feeding a respiratory gas flow from the CPAP unit towards a surface of a supply of liquid stored in a bottom portion of the liquid storage container through the respiratory gas feed opening.

18. A method according to claim 17, further comprising:
   changing a direction of the respiratory gas flow from the respiratory gas feed opening towards the surface of the liquid stored in the liquid storage container.

19. A method according to claim 18, further comprising:
   uniformly humidifying the respiratory gas flow.

20. A method according to claim 19, further comprising:
   coupling a respiration tube to the humidifying apparatus to deliver the flow of respiratory gas to the patient.

21. A method according to claim 12, wherein the respiratory gas connection portion is rigidly fixed to the CPAP unit, and the connection portion is rigidly fixed to the humidifying apparatus.

22. A humidifier assembly for a CPAP apparatus, comprising:
   a liquid container including a) a base configured to retain a body of liquid therein, at least a portion of the base being constructed of a heat conducting material, b) a top portion, and c) a seal disposed between the top portion and the base;
   a housing comprising a base portion to support the liquid container;
   a connecting structure configured to connect the housing to the CPAP apparatus and to allow communication of an outlet of the CPAP apparatus with an inlet of the housing; and
   a securing device configured to releasably interlock the housing to the CPAP apparatus upon engagement therebetween,
   wherein the base portion includes a heating element in direct contact with the heat conducting material of the base of the liquid container.

23. A humidifier assembly according to claim 22, wherein the housing defines both the inlet and an outlet communicated with an interior of the liquid container, the inlet configured to receive pressurized breathable gas and the outlet configured to deliver the pressurized breathable gas with added humidity.

24. A humidifier assembly according to claim 23, wherein the connecting structure includes contact elements that communicate with a power supply within the CPAP apparatus.

25. A humidifier assembly according to claim 24, wherein the connecting structure is configured to allow removable attachment of the CPAP apparatus to the housing.

26. A humidifier assembly according to claim 25, wherein the heat conducting material is a metallic material.

27. A CPAP apparatus including a CPAP device and the humidifier assembly according to claim 26.

28. A humidifier assembly according to claim 22, wherein the seal is positioned around a perimeter of the liquid container.

29. A humidifier assembly according to claim 28, wherein the seal is sandwiched between opposing surfaces of the top portion and the base.

30. A humidifier assembly according to claim 29, wherein the seal is in direct contact with the opposing surfaces of the top portion and the base.

31. A humidifier assembly according to claim 22, the base portion includes a heating element in direct contact with the heat conducting material of the base of the liquid container.

32. A humidifier assembly according to claim 22, wherein at least a portion of the securing device is separate from and spaced apart from the connecting structure.

33. A humidifier assembly according to claim 22, wherein the heat conducting material is adapted to conduct heat from the heating element to the liquid.

34. An apparatus for supplying a respiratory gas to a patient, comprising:
   a CPAP unit configured to generate a flow of respiratory gas; and
   a humidifying apparatus adapted to be removably coupled to the CPAP unit and humidify the flow of respiratory gas, wherein
   the CPAP unit comprises a respiratory gas connection portion on a side of the CPAP unit that is configured to be coupled to a respiration tube or the humidifying apparatus to deliver the flow of respiratory gas to the respiration tube or the humidifying apparatus, respectively,
   the humidifying apparatus comprises a connection portion on a side thereof that is configured to connect to the respiratory gas connection portion of the CPAP unit and a respiration tube connection portion configured to connect the respiration tube to the humidifying apparatus,
   each of the respiration tube connection portion of the humidifying apparatus and the respiratory gas connection portion of the CPAP unit having a respiration tube connecting member shaped to permit the respiration tube to be connected to either the CPAP unit or the humidifying apparatus,
   the humidifying apparatus further comprises a housing, a heating element provided in a bottom portion of the housing, and a liquid storage container configured to store a supply of liquid to humidify the respiratory gas flow, the liquid storage container being configured to be inserted and removed from the housing and to be in direct contact with the heating element when inserted into the housing, and
   the housing defines both an inlet and an outlet in communication with an interior of the liquid storage container, the liquid storage container being positioned between the inlet and the outlet so that the flow of respiratory gas passes through the interior of the liquid storage container before exiting through the outlet, the inlet configured to receive pressurized breathable gas and the outlet configured to deliver the pressurized breathable gas with added humidity.

35. An apparatus according to claim 34, further comprising an electrical connecting device configured to electrically couple the CPAP unit and the humidifying apparatus when the CPAP unit and the humidifying apparatus are connected by the connection portion.

36. An apparatus according to claim 35, wherein the electrical connecting device comprises an electric plug on the side of the humidifying apparatus including the connection portion and an electric terminal on the side of the CPAP unit including the respiratory gas connection portion.

37. An apparatus according to claim 36, wherein the electric terminal of the CPAP unit is located in a recess below the respiratory gas connection portion so that the electric terminal does not extend beyond a surface defined by the side of the CPAP unit.

38. An apparatus according to claim 37, further comprising a latch configured to detachably hold the CPAP unit and the humidifying apparatus when the CPAP unit and the humidifying apparatus are connected by the connection portion.

39. An apparatus according to claim 37, wherein the liquid storage container may be inserted or removed from the housing without disconnecting the respiration tube from the respiration tube connection portion.

40. An apparatus according to claim 34, wherein the humidifying apparatus further comprises a connection portion on a side of the housing that includes the inlet, the connection portion being configured to connect to the respiratory gas connection portion of the CPAP unit.

41. An apparatus according to claim 40, wherein the humidifying apparatus further comprises a humidification apparatus securing device on the side of the housing configured to releasably interlock with a CPAP securing device.

42. An apparatus according to claim 41, wherein at least a portion of the humidification apparatus securing device is located away from the connection portion.

43. An apparatus according to claim 42, wherein at least a portion of the liquid storage container is formed of heat conducting material adapted to conduct heat from the heating element to the liquid.

44. An apparatus according to claim 43, wherein the liquid storage container is configured to be inserted and removed from the housing in a cartridge-like manner.

45. An apparatus for supplying a respiratory gas under an increased pressure comprising:
   a blowing device to deliver the respiratory gas;
   a housing for the blowing device having a bottom face, a top surface face and a side face extending upwardly between the top surface region face and the bottom face; and
   a connecting device to fluidly and electrically connect the apparatus to a humidifier, the connecting device being arranged on the side face in such a way that facilitates laterally coupling the apparatus to the humidifier,
   wherein the connecting device includes a respiratory gas port structured to conduct respiratory gas to the humidifier and at least one electrical port configured to releasably connect to the humidifier and afford an electrical connection to the humidifier.

46. An apparatus as set forth in claim 45, wherein the connecting device further includes a pressure-measuring port structured to couple to a pressure-measuring conduit provided to the humidifier.

47. An apparatus as set forth in claim 46, wherein the respiratory gas port and the pressure-measuring port each include an end portion arranged in a recessed opening provided in the side face.

48. An apparatus as set forth in claim 47, wherein the recessed opening includes a sufficient depth to allow coupling of the end portion of each of the respiratory gas port and the pressure-measuring port to the peripheral apparatus.

49. An apparatus as set forth in claim 46, wherein the respiratory gas port includes a diameter that is larger than a diameter of the pressure-measuring port.

50. An apparatus as set forth in claim 46, further comprising a hose or conduit provided to the pressure-measuring port, the hose or conduit being connected to a portion of the flow path downstream from the respiratory gas port.

51. An apparatus as set forth in claim 46, wherein the respiratory gas port and the pressure-measuring port each include an end portion arranged in a recessed opening provided in the side face.

52. An apparatus as set forth in claim 51, wherein the recessed opening includes a sufficient depth to allow coupling of the end portion of each of the respiratory gas port and the pressure-measuring port to the humidifier.

53. An apparatus as set forth in claim 46, wherein the respiratory gas port includes a diameter that is larger than a diameter of the pressure-measuring port.

54. An apparatus as set forth in claim 46, wherein the pressure-measuring port is upstream of the pressure-measuring conduit when the pressure-measuring port is coupled to the pressure-measuring conduit.

55. An apparatus as set forth in claim 45, wherein the at least one electrical port is configured to afford a data connection with the humidifier.

56. An apparatus as set forth in claim 45, further comprising a securing device to releasably and laterally couple the apparatus to the humidifier, at least a portion of the securing device being positioned away from the connecting device.

* * * * *